United States Patent
Dormitzer et al.

(10) Patent No.: US 9,072,702 B2
(45) Date of Patent: Jul. 7, 2015

(54) REVERSE GENETICS USING NON-ENDOGENOUS POL I PROMOTERS

(75) Inventors: Philip Dormitzer, Weston, MA (US); Michael Franti, Blainville (CA); Peter Mason, Sommerville, MA (US); Pirada Suphaphiphat, Brookline, MA (US); Bjoern Keiner, Marburg (DE); Stefania Crotta, Cesano Maderno (IT)

(73) Assignee: Novartis AG, Basel (CH)

( * ) Notice: Subject to any disclaimer, the term of this patent is extended or adjusted under 35 U.S.C. 154(b) by 409 days.

(21) Appl. No.: 13/320,902

(22) PCT Filed: May 21, 2010

(86) PCT No.: PCT/IB2010/001332
§ 371 (c)(1),
(2), (4) Date: Apr. 5, 2012

(87) PCT Pub. No.: WO2010/133964
PCT Pub. Date: Nov. 25, 2010

(65) Prior Publication Data
US 2012/0189656 A1    Jul. 26, 2012

Related U.S. Application Data

(60) Provisional application No. 61/216,919, filed on May 21, 2009.

(51) Int. Cl.
| | | |
|---|---|---|
| C12N 7/02 | (2006.01) | |
| C12N 7/01 | (2006.01) | |
| C12N 5/10 | (2006.01) | |
| C12N 15/85 | (2006.01) | |
| A61K 39/12 | (2006.01) | |
| A61K 39/145 | (2006.01) | |

(52) U.S. Cl.
CPC ............... *A61K 39/145* (2013.01); *C12N 15/85* (2013.01); *C12N 2760/16134* (2013.01); *C12N 2760/16234* (2013.01); *C12N 2830/00* (2013.01); *C12N 2830/85* (2013.01)

(58) Field of Classification Search
CPC .......... C12N 7/00; C12N 15/85; A61K 39/12; A61K 39/145
See application file for complete search history.

(56) References Cited

U.S. PATENT DOCUMENTS

2012/0189656 A1*  7/2012  Dormitzer et al. ......... 424/204.1

FOREIGN PATENT DOCUMENTS

| WO | WO-2004078912 | 9/2004 |
| WO | WO-2007002008 | 1/2007 |

OTHER PUBLICATIONS

Heix et al. (Current Opinion in Genetics and Dvelopment. 1995; 5: 652-656).*
Wang et al. (Virology Journal. 2007; 4: 102: 1-12).*
Hoffmann et al. (PNAS. 2000; 97 (11): 6108-6113).*
Murakami (Feb. 2008). "Establishment of canine RNA polymerase I-driven reverse genetics for influenza A virus: its application for H5N1 vaccine production," J Virol. 82(3):1605-1609.
Suphaphiphat (Apr. 2010). "Human RNA Polymerase I-Driven Reverse Genetics for Influenza A Virus in Canine Cells," J Virol. 84(7): 3721-3725.
International Search Report mailed Aug. 10, 2010, for PCT Application No. PCT/IB2010/001332 filed on May 21, 2010, 3 pages.
Written Opinion dated Nov. 21, 2011, for PCT Application No. PCT/IB2010/001332 filed on May 21, 2010, 7 pages.
International Preliminary Report on Patentability dated Nov. 21, 2011, for PCT Application No. PCT/IB2010/001332 filed on May 21, 2010, 10 pages.

* cited by examiner

*Primary Examiner* — Shanon A Foley
(74) *Attorney, Agent, or Firm* — Morrison & Foerster LLP

(57) ABSTRACT

Expression of a transgene is driven in a host cell using a pol I promoter which is not endogenous to an organism from the same taxonomic order from which the host cell is derived.

20 Claims, 13 Drawing Sheets

```
AGCGTGAGCAGGAGAGAATTCTGGAGAAACAGATTGTGTTATAAGAAAGAAAGAAAGAAAG
AAGAAAGAGAAAATCCTTATGTTCTTTGAGCCTCCCCAGATTGAGTTCCTCTTCCAC
GACCTCTTCATTCAACCCAATAGACAAGTATTTGGGGAAGGGGGTCAGGTCCCAGACGCTTAA
AGGGTGGAAGTGAAAGTGGTGCGGGGAAGGGGGGGCACACCGTCTCTCCAGCGCCTTTGG
TTCAAACCTCCTTCGTGACCTCCCTCCTCCTTCGTCTTATAAATATATAAATAAAATCCT
AAGAAAAAAGAAAAAAAGGAAGGACACGAGAAAACGGTGCATCCGTTGCCGT
CCTAAGAGTCCTCGCCTGGTTTCGGCTGTTCCCTCCCTGACCTCGGAAACGTGCCTGAGTCG
TCCCGGAGCCCCGCGGAGCGCGACCCCTTTCCGGGGGGCAGGCCCGGACGGACG
GACGGACGGACGGACGGGTTTCCAAGGCTCCCGCCCCGGGAGGACGGGGGTTCGCGCGGTG
CGCGGGCCGCGTGTCTCCGGGCCCTCCGCCGTCCCGCCGGAGATCCGAGGCGCCC
TGACGCCTCGCGCCCGGATCTGTCCCGCGTCGTTCGCGCGTTGTCGGGTGCCACCTGGCG
GCCGCTTTTATAGAGCGTGTCCCCTCGGAGGCTCGGCGCGACAGGCAAGGAACAGCTTTGGTG
TCGGTTTCCCGGGCCGAGTTCCAGAGGAGGCGGCGCTCCGGGCGTCCGGCTGTCGCCG
GGGCCTCGCGCCGCGATGCGCTCGCCGAGATTGGACCTCCCGGAGCTCGAGGAGTGTCGCCG
TCGCCGCGTGTCGCCGCCGGTCCGCCTCCTCCCGCCGTCCTGGCTCGGCCGCCTCGG
GGGTCGACCAGCACCCGCGGTGTGTCTCCGCGGTGTGTCCCGGCGACCGACCTGGCCGCTCGG
GGGCGGGGACAGGGGTGGCGGCGCGACAGACCCGGCTGCGGCGCACGTGTGGGGCTCGAGGG
CCGTGTCACTCGGTTGTCTCCGTGGTCACGCCCTGCGGGCACCGGTCTGAGCCTGAGGG
GAAGCCCGTGGGTGGCGACAGACCCGGCTGCGGCGGCGCACGTGTGGGGCGTCGGAC
GCGATTTCTCCCCTTGTTCCCAGGCCCGCCTGCGGCGGCGCGTTCGGCGGTCCCGGGGCGTGC
CACGCGGGGCTGGGGCGCCGTTCGGCGGCGTCCGCcccgtggcggcgattcccggtgaggctgcctctgc
cgcgcgtggcccctccacctccctgccgagccgggttgggacggcgtaggcacggggcggtcctgaggcgcgggg
acggcctccgcacggtgctgctccggagaaactttgatgatttttcaaagtctctcccggagatcactGGCGTGGCGCGTG
GCGGGTGGGGCGTGGCCGTGGCGCGTCCACCGACCGCGTATGCCCCTCCTCACCCCC
CCCCCCCCGGTTACCTGGGCGGACCAGAAAGCCCTGGGCNGGCTCCGTGGGGTGGG
GTGGGGCGGGCGCGTGGGGCAGGTTTGGGTACAGTTGGGTGTCACGGTCCCGGAGGTCGC
GGTGACCTGTGGCTGGTCCCCGGCAGGGCGGTTATTTTCTTGCCGGAAATGAACATTTTTG
TTGCCAGGTAGGTGCTG
```

Figure 7
A
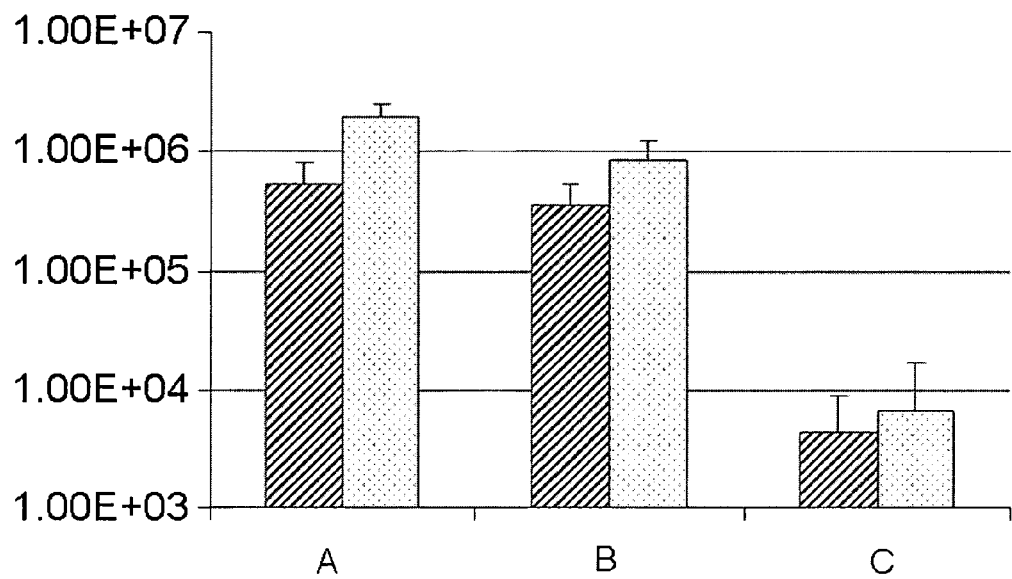
B
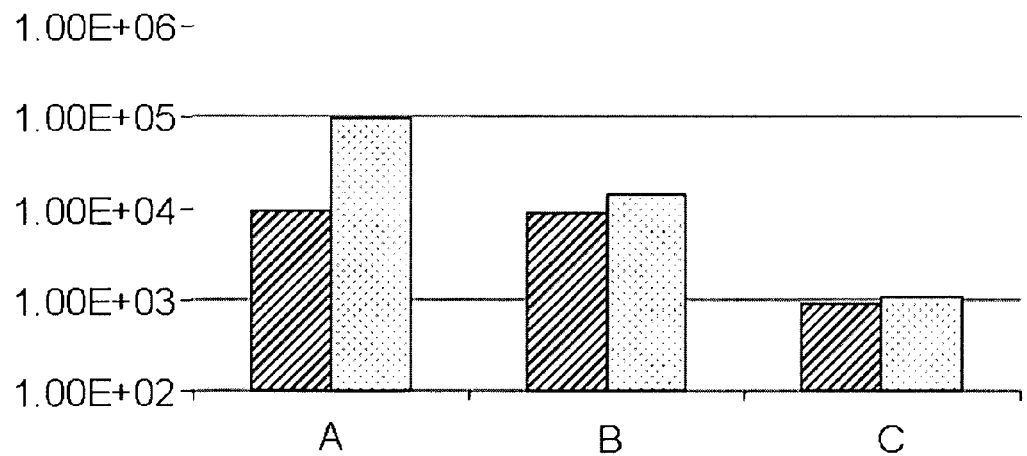

Figure 11
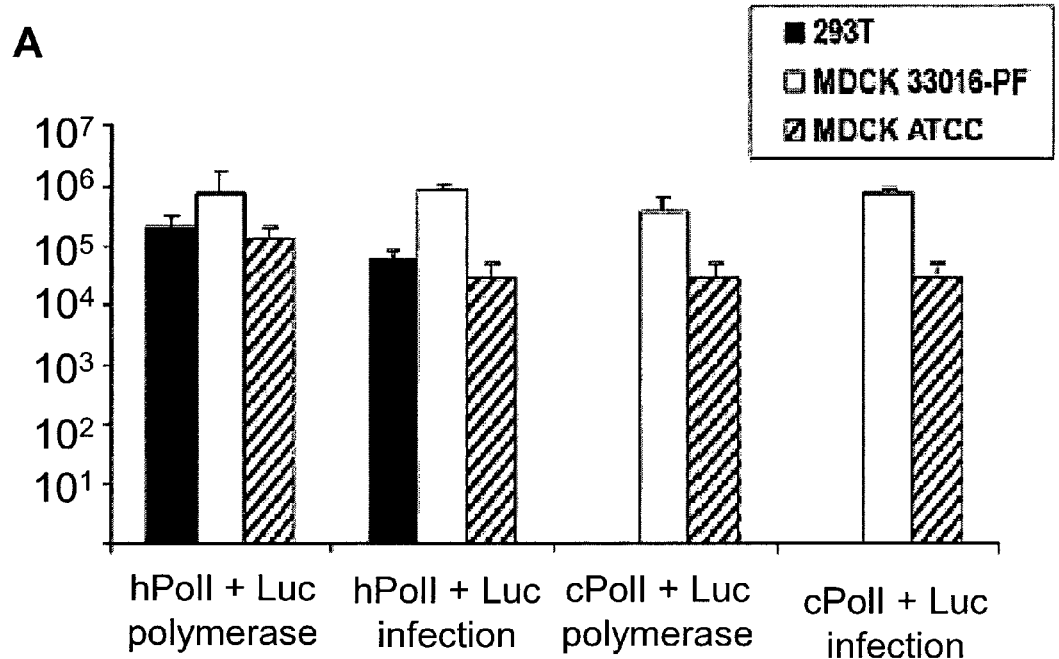
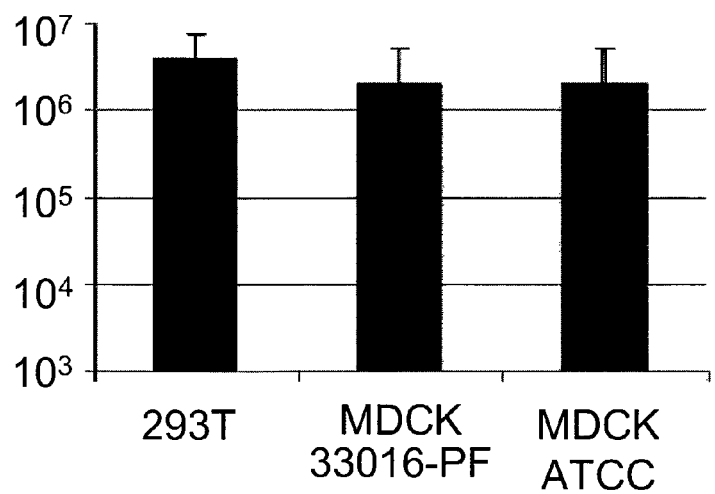

Figure 12
A
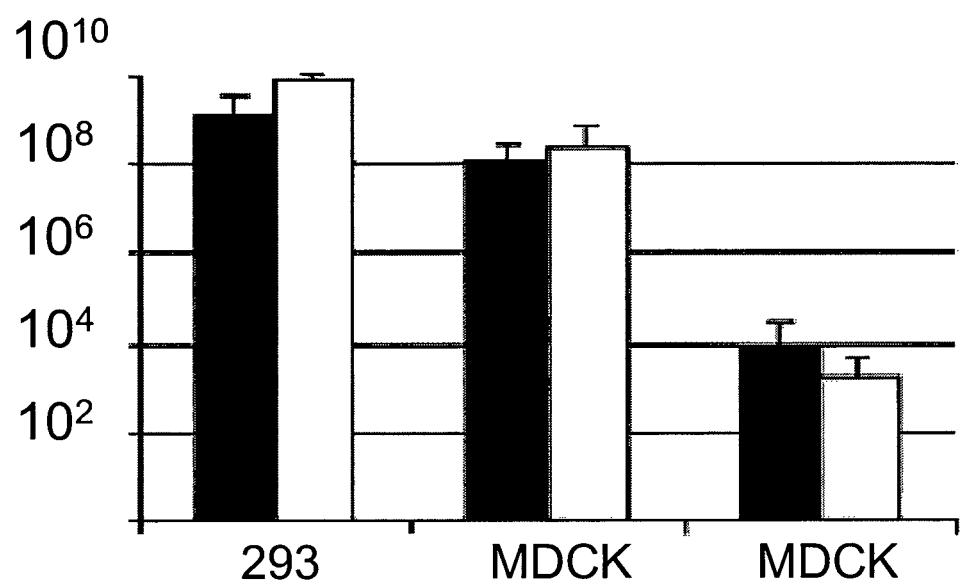
B
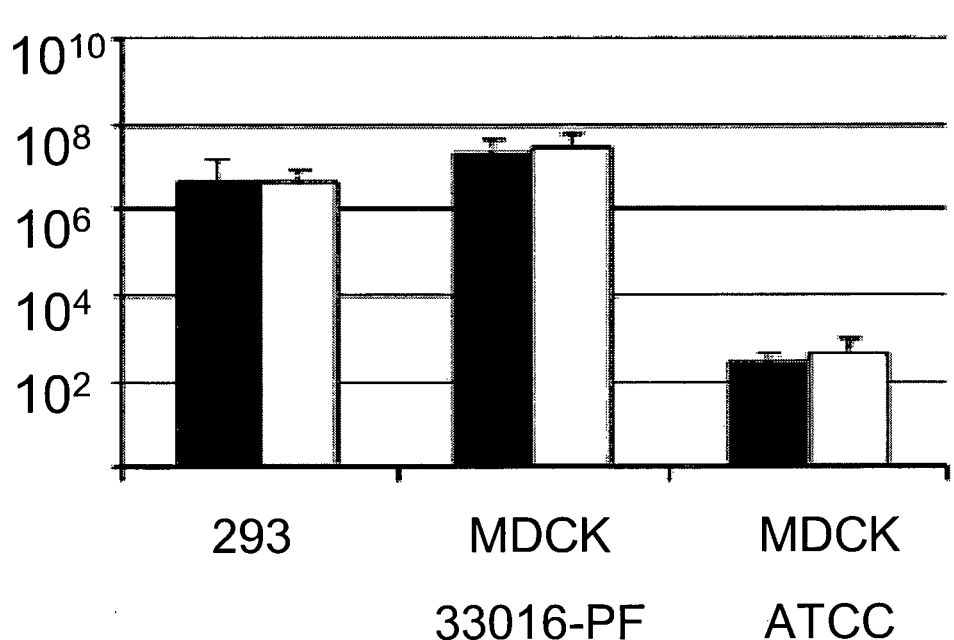

REVERSE GENETICS USING NON-ENDOGENOUS POL I PROMOTERS

CROSS REFERENCE TO RELATED APPLICATIONS

This application is a U.S. National Phase patent application of PCT/IB2010/001332, filed May 21, 2010, which claims priority to U.S. Provisional patent application Ser. No. 61/216,919 filed May 21, 2009, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002122800SEQLIST.txt, date recorded: Nov. 15, 2011, size: 22 KB).

TECHNICAL FIELD

This invention is in the field of reverse genetics. Furthermore, it relates to manufacturing vaccines for protecting against various viruses.

BACKGROUND ART

Reverse genetics permits the recombinant expression and manipulation of RNA viruses in cell culture. It is a powerful tool in virology and vaccine manufacture because it allows rapid production of recombinant viruses (including reassortants) and/or their mutation. The method involves transfecting host cells with one or more expression constructs that encode the viral genome and isolating the virus from the cells. For example, references 1 and 2 describe a method in which the influenza genomic RNA is expressed in canine cells using the canine pol I promoter. Other sources have reported the expression of influenza genomic RNA in human cells using the human pol I promoter One significant drawback of the methods of the prior art is that pol I promoters are highly species specific. For example, it has been reported that the human pol I promoter is active only in primate cells [3], and similarly that expression in canine cells would require the canine pol I promoter. Thus, where a virus needs to be grown in a cell line for which the endogenous pol I promoter has not been characterized, it has been necessary to use two different cell types for rescuing and growing the virus. However, it is desirable to avoid the use of multiple cell lines as this has the advantage, for example, that competing culture selection pressures can be avoided. The use of a single cell line for all steps of vaccine production also facilitates regulatory approval. Thus there is a continued need in the art to provide alternative methods for practising reverse genetics.

SUMMARY OF PREFERRED EMBODIMENTS

The inventors have now surprisingly discovered that it is possible to drive expression of a transgene in a host cell using a pol I promoter which is not endogenous to an organism from the same taxonomic order from which the host cell is derived.

In one embodiment, the invention provides a host cell comprising one or more expression construct(s) wherein expression of a RNA molecule from the construct(s) is controlled by a pol I promoter which is not endogenous to the host cell's order. These host cells can be used in expression systems of the invention.

The invention further provides a process for RNA expression in a host cell, comprising the steps of (i) preparing an expression construct wherein expression of a transgene of interest is driven by a pol I promoter from a first organism and (ii) introducing the expression construct of step (i) into a host cell, wherein the host cell is from a different taxonomic order from the first organism.

In a further embodiment, the invention provides a method for producing a recombinant virus wherein the virus is produced using a host cell of the invention.

The invention also provides a method of preparing a virus (e.g. for formulation into a vaccine), comprising steps of (i) producing a recombinant virus using a host cell of the invention (ii) infecting a culture host with the virus obtained in step (i), (iii) culturing the culture host from step (ii) in order to produce virus; and (iv) purifying the virus obtained in step (iii). To provide a method of preparing a vaccine, the method can then include the further step of (v) formulating the virus into a vaccine.

In addition to the non-endogenous pol I promoter(s) which are introduced as discussed above, the host cell will include endogenous pol I promoters. The non-endogenous pol I promoter(s) drive(s) expression of non-endogenous RNA, in particular viral RNA, in the cell. The invention thus provides a cell having at least one endogenous pol I promoter which control(s) expression of endogenous rRNA and at least one non-endogenous pol I promoter which control(s) expression of a viral RNA or the complement thereof.

The invention also provides a DNA expression construct encoding both a protein-coding mRNA and a viral RNA, wherein (i) the codon usage in the DNA for the protein-coding mRNA is optimised for canine cells and (ii) the viral RNA is under the control of a primate pol I promoter. The canine cells are ideally MDCK cells and the primate promoter is ideally a human pol I promoter. Expression of the protein-coding mRNA may be under the control of a pol II promoter optimised for canine cells.

Expression Constructs

The present inventors have surprisingly discovered that it is possible to drive RNA expression in a cell using a pol I promoter from an organism which is in a different taxonomic order from the cell. Thus the pol I promoter is not endogenous to an organism from the same taxonomic order from which the cell is derived. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora).

Thus in a first aspect, the invention provides a host cell comprising one or more expression construct(s) wherein expression of a RNA molecule from the construct(s) is driven by a pol I promoter which is not endogenous to the host cell's order.

In one embodiment, the host cell is a non-primate cell and the pol I promoter is a primate pol I promoter. In a specific embodiment, the host cell is a non-primate cell and the promoter is a human promoter. In a further embodiment, the host cell is a non-human cell and the pol I promoter is a human pol I promoter. In an alternative embodiment, the pol I promoter is a non-canine pol I promoter and the host cell is a canine cell. In a preferred embodiment, the host cell is a canine cell and the promoter is a primate pol I promoter. In a further preferred embodiment, the pol I promoter is a human promoter and the host cell is a canine cell (such as a MDCK cell). This embodiment is preferred as the human pol I promoter is well characterised and canine cells are often used for the production of vaccines.

The expression constructs used in the host cells may be uni-directional or bi-directional expression constructs. Where a host cell expresses more than one transgene (whether on the same or different expression constructs) it is possible to use uni-directional and/or bi-directional expression.

Bi-directional expression constructs contain at least two promoters which drive expression in different directions (i.e. both 5' to 3' and 3' to 5') from the same construct. At least one of the promoters is a non-endogenous pol I promoter as discussed herein. The two promoters can be operably linked to different strands of the same double stranded DNA. Preferably, one of the promoters is a non-endogenous pol I promoter and at least one of the other promoters is a pol II promoter. This is useful as the pol I promoter can be used to express uncapped cRNAs while the pol II promoter can be used to transcribe mRNAs which can subsequently be translated into proteins, thus allowing simultaneous expression of RNA and protein from the same construct. The pol II promoter may be endogenous or non-endogenous. Where more than one expression construct is used within an expression system, the promoters may be a mixture of endogenous and non-endogenous promoters provided that at least one of the promoters is a non-endogenous pol I promoter that can drive expression in the host cell.

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression system may contain at least two, at least three, at least four, at least five, at least six, at least seven, at least eight, at least nine, at least ten, at least eleven or at least twelve expression constructs.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. An example of a method using such linear expression constructs for the expression of influenza virus is described in reference 4.

Expression constructs of the invention can be generated using methods known in the art. Such methods were described, for example, in reference 5. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

The expression constructs of the invention can be introduced into host cells using any technique known to those of skill in the art. For example, expression constructs of the invention can be introduced into host cells by employing electroporation, DEAE-dextran, calcium phosphate precipitation, liposomes, microinjection, or microparticle-bombardment.

Where the expression host is a canine cell, such as a MDCK cell line, protein-coding regions may be optimised for canine expression e.g. using a promoter from a wild-type canine gene or from a canine virus, and/or having codon usage more suitable for canine cells than for human cells. For instance, whereas human genes slightly favour UUC as the codon for Phe (54%), in canine cells the preference is stronger (59%). Similarly, whereas there is no majority preference for Ile codons in human cells, 53% of canine codons use AUC for Ile. Canine viruses, such as canine parvovirus (a ssDNA virus) can also provide guidance for codon optimisation e.g. 95% of Phe codons in canine parvovirus sequences are UUU (vs. 41% in the canine genome), 68% of Ile codons are AUU (vs. 32%), 46% of Val codons are GUU (vs. 14%), 72% of Pro codons are CCA (vs. 25%), 87% of Tyr codons are UAU (vs. 40%), 87% of His codons are CAU (vs. 39%), 92% of Gln codons are CAA (vs. 25%), 81% of Glu codons are GAA (vs. 40%), 94% of Cys codons are UGU (vs. 42%), only 1% of Ser codons are UCU (vs. 24%), CCC is never used for Phe and UAG is never used as a stop codon. Thus protein-coding genes can be made more like genes which nature has already optimised for expression in canine cells, thereby facilitating expression.

Reverse Genetics

The expression constructs and host cells described above are particularly suitable for producing recombinant virus strains through reverse genetics techniques. The techniques can be used for the production of a wide variety of RNA viruses, including positive-strand RNA viruses [6,7], negative-strand RNA viruses [8,9] and double-stranded RNA viruses [10]. Thus, in a further aspect, the present invention provides a method for producing a recombinant virus wherein the virus is produced using an expression system as described above.

Known reverse genetics systems involve expressing DNA molecules which encode desired viral RNA (vRNA) molecules from pol I promoters, bacterial RNA polymerase promoters, bacteriophage polymerase promoters, etc. Furthermore, where a virus requires certain proteins to form an infectious virus, systems also provide these proteins e.g. the system further comprises DNA molecules that encode viral proteins such that expression of both types of DNA leads to assembly of a complete infectious virus.

Where reverse genetics is used for the expression of vRNA, it will be evident to the person skilled in the art that precise spacing of the sequence elements with reference to each other is pivotal for the polymerase to initiate replication. It is therefore important that the DNA molecule encoding the viral RNA is positioned correctly between the pol I promoter and the termination sequence, but this positioning is well within the capabilities of those who work with reverse genetics systems.

Generally, reverse genetics is suitable for expression of any viruses which are known to require production of genomic RNA during their life-cycle. Such viruses include, but are not limited to, positive-strand and negative-strand RNA viruses, such as those described below. Preferably, the virus is an orthomyxovirus, e.g., an influenza virus. The methods of the invention are further suitable for non-segmented as well as segmented viruses.

Where the virus is a positive-strand RNA virus it is often sufficient to transfect a cell with an expression construct comprising the viral genome. For example, the transfection of plasmids containing the poliovirus genome resulted in the recovery of infectious poliovirus [6,7]. Reverse genetics for negative-strand RNA viruses has presented more challenges as the antisense viral RNA is usually non-infective and requires an RNA polymerase to complete the life cycle. Thus, the viral polymerase must be supplied, either as protein or as a gene for in situ protein expression.

Where the virus requires a protein for infectivity, it is generally preferred to use bi-directional expression constructs as this reduces the total number of expression constructs required by the host cell. Thus, the method of the invention may utilise at least one bi-directional expression construct wherein a gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

In order to produce a recombinant virus, a cell must express all segments of the viral genome which are necessary to assemble a virion. DNA cloned into the expression constructs of the present invention preferably provides all of the viral RNA and proteins, but it is also possible to use a helper virus to provide some of the RNA and proteins, although systems which do not use a helper virus are preferred. Where the virus is a non-segmented virus this can usually be achieved by utilising a single expression construct in the method of the invention, even though it is also within the scope of the invention to express the viral genome of non-segmented viruses using more than one expression construct. Where the virus is a segmented virus, the viral genome is usually expressed using more than one expression construct in the method of the invention. However, it is also envisioned to combine one or more segments or even all segments of the viral genome on a single expression construct.

Methods of the invention are particularly suitable for the production of reassortant virus strains. The technique can use in vitro manipulation of plasmids to generate combinations of viral segments, to facilitate manipulation of coding or non-coding sequences in the viral segments, to introduce mutations, etc. The use of the expression system for the production of reassortant virus strains is preferred as this can significantly decrease the time needed to obtain a reassortant seed virus which is particularly beneficial in situations where a rapid production of vaccine is needed to counteract an epidemic. Thus, it is preferred that the method of this aspect of the invention uses one or more expression constructs that express viral genes from or derived from at least two different wild type strains.

In some embodiments an expression construct will also be included which leads to expression of an accessory protein in the host cell. For instance, it can be advantageous to express a non-viral serine protease (e.g. trypsin) as part of a reverse genetics system.

When the expression constructs of the invention are used for the expression of influenza A viral segments, it is possible to generate the expression construct by introducing the influenza A viral segment into an expression construct comprising a negative selection marker (for example, ccdB) and the highly conserved influenza A virus gene termini [11]. The advantage of this is that no restriction sites are required and that any influenza A viral segment can be cloned provided it has termini which are complementary to the gene termini on the expression construct.

Cells

The present invention can be practised with any eukaryotic or prokaryotic cell that can produce the virus of interest. The invention will typically use a cell line although, for example, primary cells may be used as an alternative. The cell will typically be mammalian. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [12-14]. Suitable dog cells are e.g. kidney cells, as in the CLDK and MDCK cell lines.

Further suitable cells include, but are not limited to: CHO; 293T; BHK; MRC 5; PER.C6 [15]; FRhL2; WI-38; etc. Suitable cells are widely available e.g. from the American Type Cell Culture (ATCC) collection [16], from the Coriell Cell Repositories [17], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940.

Preferred cells (particularly for growing influenza viruses) for use in the invention are MDCK cells [18-20], derived from Madin Darby canine kidney. The original MDCK cells are available from the ATCC as CCL 34. It is preferred that derivatives of these cells or other MDCK cells are used. Such derivatives were described, for instance, in reference 18 which discloses MDCK cells that were adapted for growth in suspension culture ('MDCK 33016' or '33016-PF', deposited as DSM ACC 2219; see also ref. 18). Furthermore, reference 21 discloses MDCK-derived cells that grow in suspension in serum free culture ('B-702', deposited as FERM BP-7449). In some embodiments, the MDCK cell line used may be tumorigenic. It is also envisioned to use non-tumorigenic MDCK cells. For example, reference 22 discloses non tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 23 discloses MDCK cells with high susceptibility to infection, including 'MDCK.5F1' cells (ATCC CRL 12042).

It is possible to use a mixture of more than one cell type to practise the methods of the present invention. However, it is preferred that the methods of the invention are practised with a single cell type e.g. with monoclonal cells. Preferably, the cells used in the methods of the present invention are from a single cell line. Furthermore, the same cell line may be used for rescuing the virus and for any subsequent propagation of the virus.

Preferably, the cells are cultured in the absence of serum, to avoid a common source of contaminants. Various serum-free media for eukaryotic cell culture are known to the person skilled in the art (e.g. Iscove's medium, ultra CHO medium (BioWhittaker), EX-CELL (JRH Biosciences)). Furthermore, protein-free media may be used (e.g. PF-CHO (JRH Biosciences)). Otherwise, the cells for replication can also be cultured in the customary serum-containing media (e.g. MEM or DMEM medium with 0.5% to 10% of fetal calf serum).

The cells may be in adherent culture or in suspension.

Screening for Suitable Cell Lines

Suitable cells for use in accordance with the present invention are widely available. Furthermore, it is possible to screen for further cells using techniques commonly known in the art. Screening for suitable cells may be necessary, for example, where a new pol I promoter is identified and where it is desirable to find cell lines which will support expression by the new promoter. Likewise, where a new cell is isolated, it may be necessary to confirm which pol I promoters can drive expression in it.

Suitable techniques for screening cells will be evident to those of skill in the art. For example, a reporter gene can be cloned under control of the pol I promoter of interest and the construct can be transfected into the cell line which is to be screened. In such experiments, cells transfected with a construct that contains the reporter gene but lacks a promoter sequence can be used as a control. Thus, where the expression of the gene in a test sample (e.g. cells containing a transgene under control of the pol I promoter of interest) is significantly higher than the expression in the control (e.g. cells containing the same transgene as the test sample but where the transgene does not contain a promoter to drive expression of the transgene), the cell line is suitable for use with that promoter according to the invention. Expression of the transgene can be measured, for example, by reverse transcribing the transgene RNA and subjecting the obtained cDNA to real-time PCR. Alternatively, it is also possible to clone a reporter gene (e.g. GFP, YFP, luc etc.) in antisense direction under control of the pol I promoter. A transcript from such a construct may then be transcribed into mRNA by a viral polymerase and subsequently be translated into a protein. Thus, any cell which expresses the reporter gene can be easily identified by the presence of the reporter gene product.

It is further possible to adapt cells in which a foreign pol I would not normally drive expression to obtain cells in which the pol I promoter can drive expression. This can be achieved, for example, by subjecting the cells to growth conditions which would not normally be suitable for them. For example, a cell line which would normally grow only adherently can be held artificially in suspension and the cells which continue to grow under these conditions can be propagated further. Alternatively, it is possible to adherently culture cells that would normally grow in suspension, e.g. by using high binding plastic culture vessels or by adding serum to the culture. Similarly, it is possible to grow cells which normally require serum for their growth under serum-free conditions or, conversely, to expose cells which are adapted to serum-free growth to serum. The selected cells can then be assayed for activity of the pol I promoter, as described earlier. Further suitable growth parameters which can be altered in this manner will be apparent to those of skill in the art and include, but are not limited to, temperature, pH, pO$_2$, serum concentration, etc. Furthermore, the cells can be subjected to physical or chemical treatments, such as UV radiation or to chemical mutagens. Likewise, it is possible to screen for new properties of cells which have merely been passaged under normal culture conditions.

For example, reference 18 describes a method in which MDCK cells (usually adherent) were adapted to growth in suspension under serum-free conditions. Starting cells were cultivated in serum-free medium in roller bottles under conditions which are normally used to cultivate cells that grow in suspension. Following several passages under these selective conditions, several cell lines were obtained that could grow in suspension in serum-free medium. One example is the 33016 cell line (deposited as DSM ACC 2219). The inventors have demonstrated that a human pol I promoter can drive expression of a reporter gene in these MDCK cells.

RNA Polymerase I Promoters

Most reverse genetics methods use expression vectors which comprise a RNA polymerase I (RNA pol I) promoter to drive transcription of viral genomic RNA. The pol I promoter gives a transcript with unmodified 5' and 3' ends which is necessary for full infectivity of many viruses e.g. influenza.

Natural pol I promoters are bipartite, having two separate regions: the core promoter and the upstream promoter element (UPE). Although this general organisation is common to pol I promoters from most species, however, the actual sequences of the promoters vary widely. The core promoter surrounds the transcription startpoint, extending from about −45 to +20, and is sufficient to initiate transcription. The core promoter is generally GC rich. Although the core promoter alone is sufficient to initiate transcription, the promoter's efficiency is very much increased by the UPE. The UPE typically extends from about −180 to −107 and is also GC rich. The activity of the promoter may be further enhanced by the presence of distal enhancer-like sequences, which might function by stabilizing the pre-initiation complex.

The sequence of the pol I promoter has been identified in a variety of species, including human, dog and chicken. The invention uses a pol I promoter which is not endogenous to an organism in the same taxonomic order as the host cell. The terms "endogenous" and "non-endogenous" are thus used in relation to the host cell and the pol I promoter which is present in an expression construct. The inter-species sequence variation in pol I promoters means that it is simple to determine whether any particular pol I promoter in a cell is endogenous or non-endogenous. Thus the invention may utilise the human, dog or chicken pol I promoter for RNA expression in a host cell which is not derived from the same taxonomic order as the pol I promoter (e.g. a primate pol I promoter in a canine host cell). Sequence comparisons, either in silico or experimental, can be used to confirm the organism from which any particular pol I promoter is derived e.g. FIG. 10 shows an alignment of the canine and human pol promoters up to the transcription start site, with <60% sequence identity.

Expression constructs of the invention include at least one core promoter; preferably they also include at least one UPE, and they may also include one or more enhancer elements. It is also possible to use the fragments of natural promoters, provided that these fragments can initiate transcription. For example, FIG. 3 shows the sequence of the full-length canine pol I promoter (SEQ ID NO: 3) and various fragments which are sufficient to drive expression of a transgene (see also FIG. 4 and SEQ ID NOs: 4 and 5). Furthermore, FIG. 2 shows the sequence of the human pol I promoter (SEQ ID NO: 1) and a fragment of it which alone is sufficient for transgene expression in the host cell (see also FIG. 5 and SEQ ID NO: 2).

A human pol I promoter which can be used according to the invention may comprise the sequence of SEQ ID NO: 1 or SEQ ID NO: 2, or a variant thereof. Where a canine promoter is used according to the invention, it may comprise the sequence of SEQ ID NO: 3, SEQ ID NO: 4 or SEQ ID NO: 5, or a variant thereof.

The pol I promoter may comprise (i) a sequence having at least p % sequence identity to any of SEQ ID NOs: 1 to 5, and/or (ii) a fragment any of SEQ ID NOs: 1 to 5, provided that the promoter has the ability to initiate and drive transcription of an operatively linked RNA-encoding sequence in a host cell of interest. The value of p may be 75, 80, 85, 90, 95, 96, 97, 98, 99 or more. The fragment may itself be of sufficient length to drive expression (e.g. SEQ ID NO: 4 is a fragment of SEQ ID NO: 3) or the fragment may be joined to other sequences and this combination will drive expression. The ability of such pol I promoters to drive expression in a host cell of interest can readily be assessed e.g. using the assays described above with an antisense reporter gene under control of the promoter.

Virus Preparation

In a further aspect, the present invention provides a method of preparing a virus for vaccine manufacture, comprising steps of (i) producing a recombinant virus as described herein (ii) infecting a culture host with the virus obtained in step (i), (iii) culturing the host from step (iii) in order to produce virus; (iv) purifying the virus obtained in step (iii) and (optionally) (v) formulating the virus into a vaccine.

Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. In step (iii), the cells are preferably cultured at a temperature of between 30° C. and 36° C. or between 32° C. and 34° C. or at 33° C. This is particularly preferred where the method of the invention is used to produce influenza virus, as it has been shown that incubation of infected cells in this temperature range results in production of a virus that results in improved efficacy when formulated into a vaccine [24].

The oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8\text{-}25 \times 10^5$ cells/mL in the batch system or preferably about $5\text{-}20 \times 10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. In some embodiments, the cells may thus be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The viruses isolated in step (i) can also be grown on eggs in step (ii). The current standard method for influenza virus growth for vaccines uses embryonated SPF hen eggs, with virus being purified from the egg contents (allantoic fluid). It is also possible to passage a virus through eggs and subsequently propagate it in cell culture.

Viruses

The methods of the invention may be practised with any virus which can be expressed by reverse genetics in a cell. Such viruses can be segmented or non-segmented viruses. Furthermore, the virus can be a positive-strand RNA virus or a negative-strand virus. In a further embodiment, the virus may also be a double-stranded RNA virus.

Where the virus is a negative-strand RNA virus, the virus may be from a family selected from the group consisting of Paramyxoviridae, Pneumovirinae, Rhabdoviridae, Filoviridae, Bornaviridae, Orthomyxoviridae, Bunyaviridae, or Arenaviridae. Furthermore, the virus may be a virus from a genus selected from the group consisting of Paramyxovirus, Orthomyxovirus, Respirovirus, Morbillivirus, Rubulavirus, Henipaviras, Avulavirus, Pneumovirus, Metapneumovirus, Vesiculovirus, Lyssavirus, Ephemerovirus, Cytorhabdovirus, Nucleorhabdovirus, Novirhabdovirus, Marburgvirus, Ebolavirus, Bornavirus, Influenzavirus A, Influenzavirus B, Influenzavirus C, Thogotovirus, Isavirus, Orthobunyavirus, Hantavirus, Nairovirus, Phlebovirus, Tospovirus, Arenavirus, Ophiovirus, Tenuivirus, or Deltavirus. In specific embodiments, the negative-strand RNA virus is selected from the group consisting of Sendai virus, Measles virus, Mumps virus, Hendra virus, Newcastle disease virus, Human respiratory syncytial virus, Avian pneumovirus, Vesicular stomatitis Indiana virus, Rabies virus, Bovine ephemeral fever virus, Lettuce necrotic yellows virus, Potato yellow dwarf virus, Infectious hematopoietic necrosis virus, Lake Victoria marburgvirus, Zaire ebolavirus, Borna disease virus, Influenza virus, Thogoto virus, Infectious salmon anemia virus, Bunyamwera virus, Hantaan virus, Dugbe virus, Rift Valley fever virus, Tomato spotted wilt virus, Lymphocytic choriomeningitis virus, Citrus psorosis virus, Rice stripe virus, and Hepatitis delta virus. In preferred embodiments, the virus is an influenza virus (see below).

Where the virus is a positive-strand RNA virus, the virus may be from a family selected from the group consisting of Arteriviridae, Coronaviridae, Picornaviridae and Roniviridae. Furthermore, the virus may be a virus from a genus selected from the group consisting of Arterivirus, Coronavirus, Enterovirus, Torovirus, Okavirus, Rhinovirus, Hepatovirus, Cardiovirus, Aphthovirus, Parechovirus, Erbovirus, Kobuvirus and Teschovirus. In specific embodiments, the virus is selected from the group consisting of severe acute respiratory syndrome (SARS) virus, polio virus, Human enterovirus A (HEV-A), Human enterovirus B (HEV-B), Human enterovirus C, Human enterovirus D, Hepatitis A and Human rhinovirus A and B.

Where the virus is a double-stranded RNA virus, the virus may be from a family selected from the group consisting of Birnaviridae, Cystoviridae, Hypoviridae, Partitiviridae, Reoviridae and Totiviridae. Furthermore, the virus may be a virus from a genus selected from the group consisting of Aquabirnavirus, Avibirnavirus, Entomobirnavirus, Cystovirus, Partitivirus, Alphacryptovirus, Betacryptovirus, Aquareovirus, Coltivirus, Cypovirus, Fijivirus, Idnoreovirus, Mycoreovirus, Orbivirus, Orthoreovirus, Oryzavirus, Phytoreovirus, Rotavirus and Seadornavirus.

The present invention is particularly suitable for viruses which undergo rapid mutation and where the recombinant approach allows for a more rapid isolation of the virus which can then be further propagated to obtain suitable vaccines. Therefore, in a preferred embodiment the virus is influenza.

Influenza Viruses

Influenza viruses are particularly suitable for use in the methods of the present invention, particularly influenza A viruses and influenza B viruses, as reverse genetics for this virus has been well characterized. Influenza viruses are segmented negative strand RNA viruses. Influenza A and B viruses have eight segments, whereas influenza C virus has seven. The virus requires at least four viral proteins (PB1, PB2, PA and nucleoprotein) to initiate replication and transcription.

Reverse genetics for influenza A and B viruses can be practised with 12 plasmids to express the four required proteins and all eight genome segments. To reduce the number of constructs, however, a plurality of RNA polymerase I transcription cassettes (for viral RNA synthesis) can be included on a single plasmid (e.g. sequences encoding 1, 2, 3, 4, 5, 6, 7 or all 8 influenza vRNA segments), and a plurality of protein-coding regions with RNA polymerase II promoters on another plasmid (e.g. sequences encoding 1, 2, 3, 4, 5, 6, 7 or 8 influenza mRNA transcripts) [25]. It is also possible to include one or more influenza vRNA segments under control of a pol I promoter and one or more influenza protein coding regions under control of another promoter, in particular a pol II promoter, on the same plasmid. As described above, this is preferably done by using bi-directional plasmids. Preferred aspects of the reference 25 method involve: (a) PB1, PB2 and PA mRNA-encoding regions on a single plasmid; and (b) all 8 vRNA encoding segments on a single plasmid. Including the neuraminidase (NA) and hemagglutinin (HA) segments on one plasmid and the six other segments on another plasmid is particularly preferred as newly emerging influenza virus strains usually have mutations in the NA and/or HA segments. Therefore, in this embodiment, only the vector comprising the HA and NA sequence needs to be replaced.

Preferred expression systems for influenza A viruses encode genome segments derived from a plurality of different wild-type strains. The system may encode 1 or more (e.g. 1, 2, 3, 4, 5 or 6) genome segments from a PR/8/34 strain (A/Puerto Rico/8/34), but usually this/these will not include the PR/8/34 HA segment and usually will not include the PR/8/34 NA segment. Thus the system may encode at least one of segments NP, M, NS, PA, PB1 and/or PB2 (possibly all six) from PR/8/34.

Other useful expression systems for influenza A viruses may encode 1 or more (e.g. 1, 2, 3, 4, 5 or 6) genome segments from an AA/6/60 influenza virus (A/Ann Arbor/6/60), but usually this/these will not include the AA/6/60 HA segment and usually will not include the AA/6/60 NA segment. Thus the system may encode at least one of segments NP, M, NS, PA, PB1 and/or PB2 (possibly all six) from AA/6/60.

The system may encode 1 or more genome segments from an A/California/4/09 strain e.g. the HA segment and/or the NA segment. Thus, for instance, the HA gene segment may encode a H1 hemagglutinin which is more closely related to SEQ ID NO: 6 than to SEQ ID NO: 7 (i.e. has a higher degree sequence identity when compared to SEQ ID NO: 6 than to SEQ ID NO: 7 using the same algorithm and parameters). SEQ ID NOs: 6 and 7 are 80% identical. Similarly, the NA gene may encode a N1 neuraminidase which is more closely related to SEQ ID NO: 8 than to SEQ ID NO: 9. SEQ ID NOs: 8 and 9 are 82% identical.

Expression systems for influenza B viruses may encode genome segments derived from a plurality of different wild-type strains. The system may encode 1 or more (e.g. 1, 2, 3, 4, 5 or 6) genome segments from a AA/1/66 influenza virus (B/Ann Arbor/1/66), but usually this/these will not include the AA/I/66 HA segment and usually will not include the AA/1/66 NA segment. Thus the system may encode at least one of segments NP, M, NS, PA, PB1 and/or PB2 from AA/1/66.

Viral segments and sequences from the A/PR/8/34, AA/6/60, AA/1/66, A/Chile/1/83 and A/California/04/09 strains are widely available. Their sequences are available on the public databases e.g. GI:89779337, GI:89779334, GI:89779332, GI:89779320, GI:89779327, GI:89779325, GI:89779322, GI:89779329.

A reverse genetics system for influenza virus may include an expression construct which leads to expression of an accessory protein in the host cell. For instance, it can be advantageous to express a non-viral serine protease (e.g. trypsin).

Vaccine

The method of the third aspect of the invention utilises virus produced according to the method to produce vaccines.

Vaccines (particularly for influenza virus) are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce sub-virion preparations, including the 'Tween-ether' splitting process. Methods of splitting influenza viruses, for example are well known in the art e.g. see refs. 26-31, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkyl thioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

The method of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 32). Live viruse vaccines include MedImmune's FLUMIST™ product (trivalent live virus vaccine).

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [33] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membraneglycoproteins to excess amounts of phospholipids, to give liposomes with viral proteins in their membrane.

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [34,35]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 45, about 30, about 15, about 10, about 7.5, about 5, about 3.8, about 3.75, about 1.9, about 1.5, etc. per strain. For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

Influenza virus strains for use in vaccines change from season to season. In inter-pandemic periods, vaccines typically include two influenza A strains (H1N1 and H3N2) and one influenza B strain, and trivalent vaccines are typical. The invention may also use pandemic viral strains (i.e. strains to which the vaccine recipient and the general human population are immunologically nave, in particular of influenza A virus), such as H2, H5, H7 or H9 subtype strains, and influenza vaccines for pandemic strains may be monovalent or may be based on a normal trivalent vaccine supplemented by a pandemic strain. Depending on the season and on the nature of the antigen included in the vaccine, however, the invention may protect against one or more of HA subtypes H1, H2, H3, H4, H5, H6, H7, H8, H9, H10, H11, H12, H13, H14, H15 or H16. The invention may protect against one or more of influenza A virus NA subtypes N1, N2, N3, N4, N5, N6, N7, N8 or N9.

As well as being suitable for immunizing against inter-pandemic strains, the compositions of the invention are particularly useful for immunizing against pandemic or potentially-pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. 1-15, H6 or H9, that have generally been found only in bird populations), such that the human population will be immunologically naïve to the strain's hemagglutinin; (b) it is capable of being transmitted horizontally in the human population; and (c) it is pathogenic to humans. A virus with H5 hemagglutinin type is preferred for immunizing against pandemic influenza, such as a H5N1 strain. Other possible strains include H5N3, H9N2, H2N2, H7N1 and H7N7, and any other emerging potentially pandemic strains. The invention is particularly suitable for protecting against potential pandemic virus strains that can or have spread from a non-human animal population to humans, for example a swine-origin H1N1 influenza strain. The invention is then suitable for vaccinating humans as well as non-human animals.

Other strains whose antigens can usefully be included in the compositions are strains which are resistant to antiviral therapy (e.g. resistant to oseltamivir [36] and/or zanamivir), including resistant pandemic strains [37].

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [38], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 39.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 μg/ml) mercurial material e.g. thiomersal-free [30,40]. Vaccines containing no mercury are more preferred. α-tocopherol succinate can be included as an alternative to mercurial compounds [30]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [41], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any oncogenic activity of the DNA.

Thus a vaccine composition prepared according to the invention preferably contains less than 10 ng (preferably less than 1 ng, and more preferably less than 100 μg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 42 & 43, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [44].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [45].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [46-48], as described in more detail in Chapter 10 of ref. 49 and chapter 12 of ref. 50. The MF59 emulsion advantageously includes citrate ions e.g. 10 mM sodium citrate buffer.

An emulsion of squalene, DL-α-tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [51].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [52] (0.05-1% Thr-MDP, 5% squalane, 2.5% Pluronic L121 and 0.2% polysorbate 80). It can also be used without the Thr-MDP, as in the "AF" adjuvant [53] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [54]. The emulsion may also include one or more of: alditol; a cryoprotective agent (e.g. a sugar, such as dodecylmaltoside and/or sucrose); and/or an alkylpolyglycoside. The emulsion may include a TLR4 agonist [55]. Such emulsions may be lyophilized.

An emulsion of squalene, poloxamer 105 and Abil-Care [56]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 57, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 58, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion in which a saponin (e.g. QuilA or QS21) and a sterol (e.g. a cholesterol) are associated as helical micelles [59].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [60].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [60].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [61]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [62-64], oral [65], intradermal [66, 67], transcutaneous, transdermal [68], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated H. influenzae type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

BRIEF DESCRIPTION OF THE DRAWINGS

FIG. 2 shows the full-length (FL) human pol I promoter sequence (SEQ ID NO: 1). The pHW2000 human Pol I Promoter sequence (SEQ ID NO: 2; "short" human pol I promoter)) within the full-length sequence is shown in underlined fonts. The arrow indicates the transcriptional start site.

FIG. 3 shows the full-length (FL) canine pol I promoter sequence (NW_878945; SEQ ID NO: 3). The SHORT promoter sequence within the full-length promoter sequence is shown in underlined capital fonts (SEQ ID NO: 5); the MID promoter sequence within the full-length promoter sequence is shown in underlined capital fonts and bold lowercase fonts (SEQ ID NO: 4);

FIG. 7 shows the activity of the human pol I promoter (dotted columns) and the canine pol I promoter (cross-hatched columns) in MDCK 33016 cells (FIG. 7A) and in MDCK ATCC cells (FIG. 7B). A indicates LUC+polymerasse, B indicates LUC+infection and C shows LUC only. The y-axis indicates relative light units (RLU).

FIG. 11A shows the expression levels of a reporter transgene under control of the human pol I (hPolI) promoter or canine polI promoter (cPolI) in MDCK ATCC, MDCK 33016-PF and 293T cells. The black columns represent the results with 293T cells, the white columns show the results with MDCK 33016-PF and the cross-hatched columns represent the results with MDCK ATCC cells;

FIG. 11B compares the transfection efficiency in human and canine cells. The y-axis in both graphs indicates relative light units (RLUs).

FIG. 12 shows the rescue of the A/Puerto Rico/8/34 influenza strain by human polI promoter-based reverse genetics in MDCK ATCC, MDCK 33016-PF and 293T cells in the presence (white columns) and absence (black columns) of the TMPRSS2 helper plasmid and with (black columns) and without (white columns) addition of feeder cells (12B). The y-axis represents the virus titre (ffu/mL).

BRIEF DESCRIPTION OF SEQUENCE LISTING

SEQ ID NO: 1 is the full-length (FL) human pol I promoter sequence
SEQ ID NO: 2 is the pHW2000 human Pol I promoter sequence
SEQ ID NO: 3 is the full-length (FL) canine pol I promoter sequence
SEQ ID NO: 4 is the MID canine pol I promoter sequence
SEQ ID NO: 5 is the SHORT canine pol I promoter sequence
SEQ ID NO: 6 is the HA sequence from A/California/04/09
SEQ ID NO: 7 is the HA sequence from A/Chile/1/1983
SEQ ID NO: 8 is the NA sequence from A/California/04/09
SEQ ID NO: 9 is the NA sequence from A/Chile/1/1983

MODES FOR CARRYING OUT THE INVENTION

The Human Pol I Promoter is Active in Human as Well as Canine Cells

Figure 1:
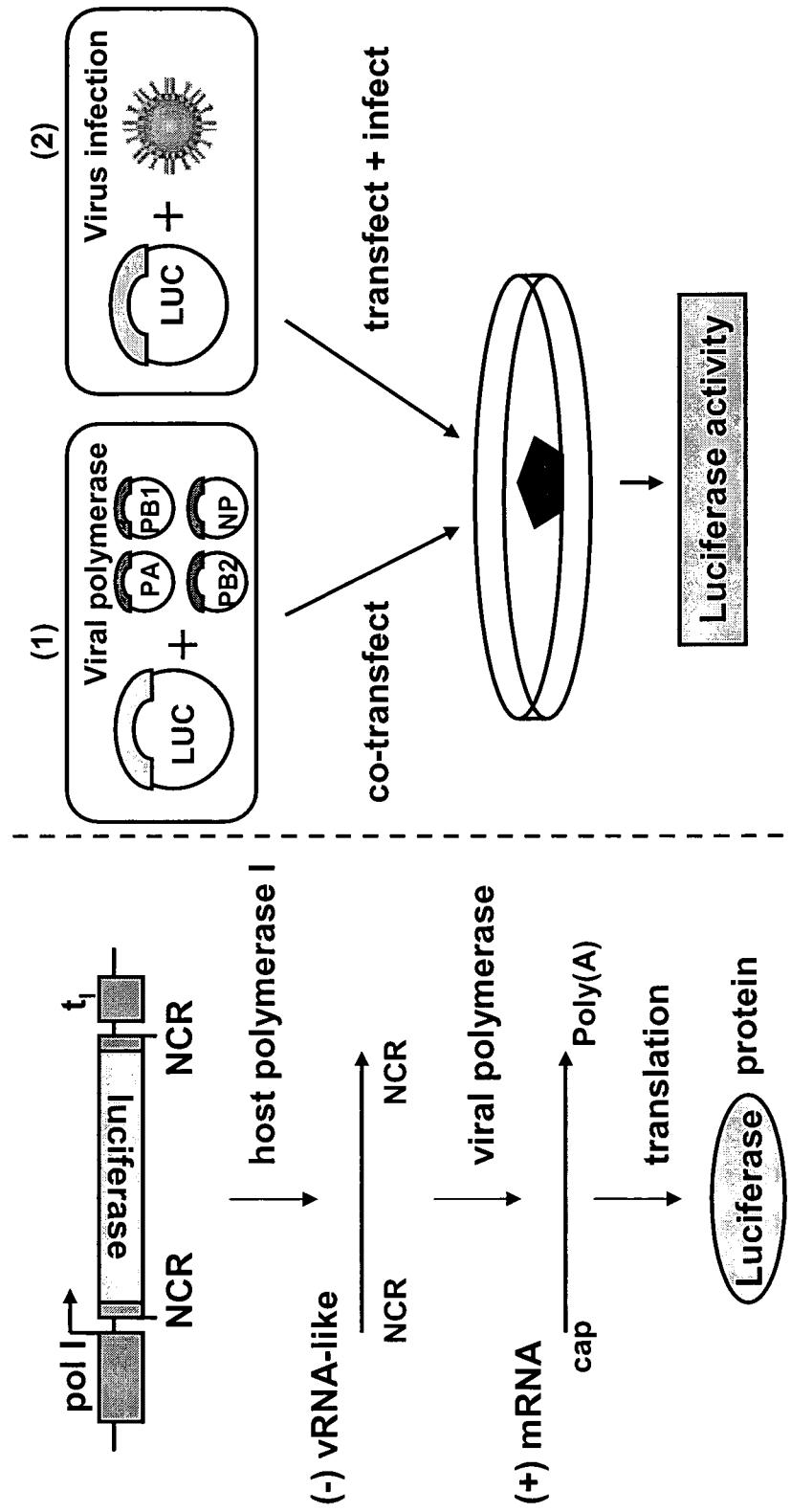
FIG. 1 illustrates the expression construct which was used for assaying pol I promoter activity with a luciferase reporter.

In order to assess the activity of the pol I promoter in non-endogenous host cells, MDCK cells were transfected with an expression construct which allows expression of a luciferase (luc) RNA in antisense direction under control of a 487 bp fragment of the human pol I promoter or various fragments of the canine pol I promoter (as shown in FIG. 3). The expressed RNA can be transcribed into mRNA by a viral polymerase and subsequently be translated into luc protein. Thus, cells expressing the transgene can be easily identified by assaying for luciferase activity. In order for the assay to work it is necessary to provide viral polymerase. This can be achieved by co-transfecting the cell with expression constructs which encode the viral polymerase or, alternatively, infecting the transfected cell with a helper virus. The assay is illustrated in FIG. 1.

FIG. 11A shows that the human pol I promoter is able to drive expression of the transgene in MDCK ATCC cells and also in MDCK 33016-PF cells with the same efficiency as the canine pol I promoter. The expression levels of the transgene with the human pol I promoter in MDCK ATCC cells are even higher than those observed in human 293T cells. In order to confirm that the transfection efficiency of the tested cell types are comparable, they were transfected with a construct containing a luciferase gene under control of a CMV promoter. The level of luciferase activity was measured. The results are shown in FIG. 11B and confirm that the transfection efficiency of the tested cells is comparable.

Figure 4:
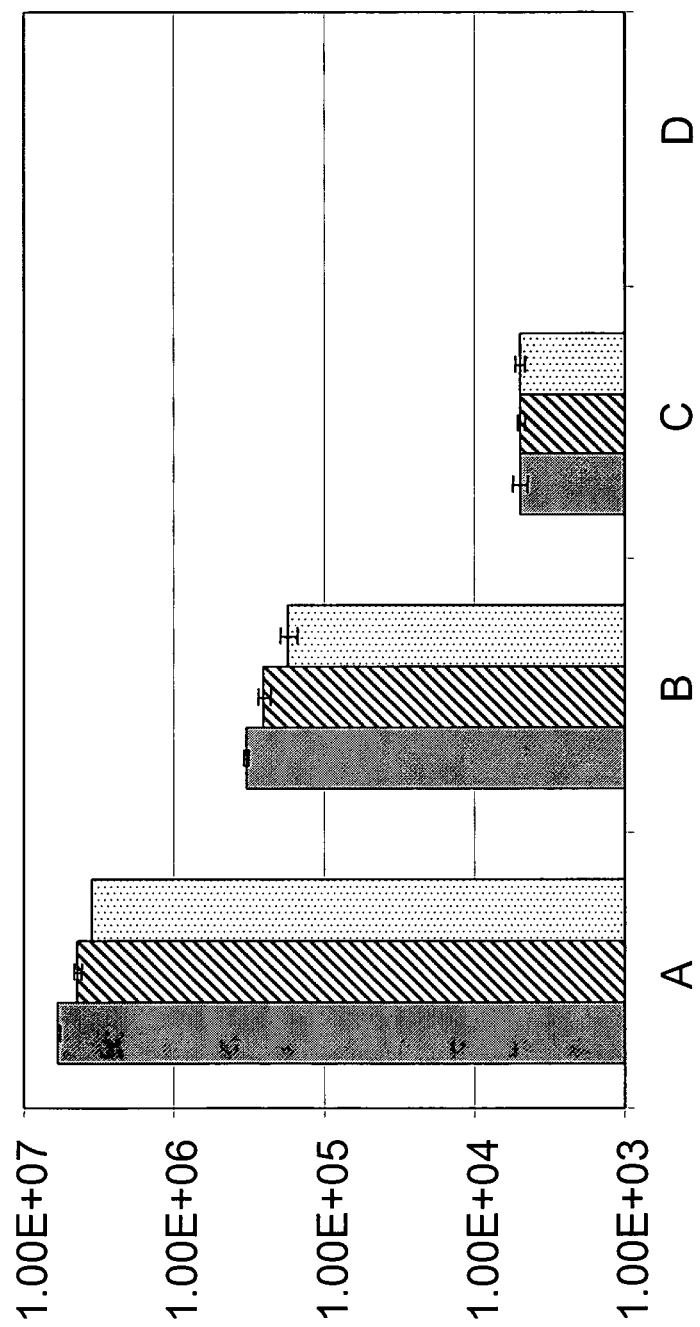
FIG. 4 shows canine pol I promoter activity in MDCK cells. The solid grey columns show the results with the FL canine pol I promoter, the cross-hatched columns show the results with the MID canine promoter and the dotted columns show the results with the SHORT canine pol I promoter. "A" indicates LUC and viral polymerase, "B" indicates LUC and infection (MOI=0.05), "C" indicates LUC and "D" is no DNA. The y-axis indicates relative light units (RLU).
Figure 5:
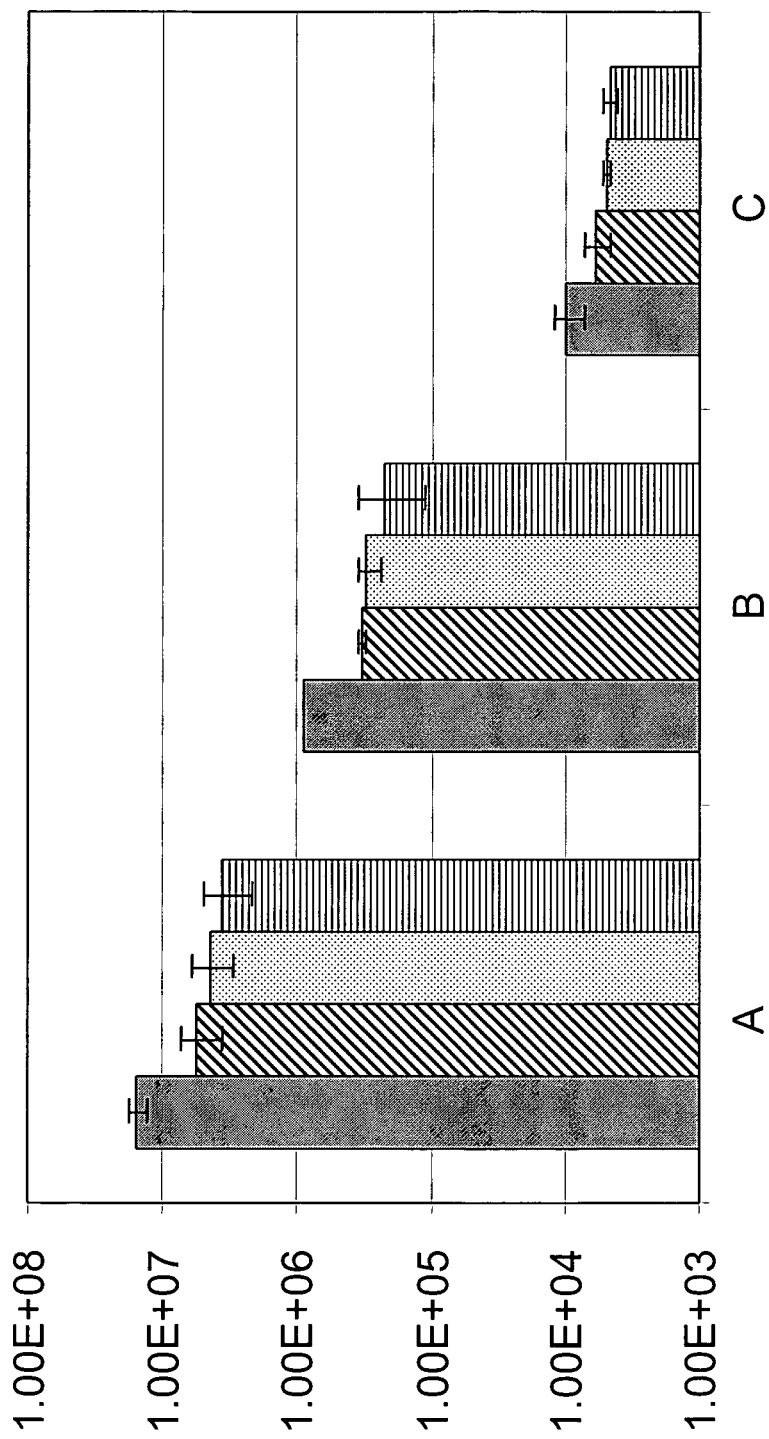
FIG. 5 shows human pol I promoter activity in MDCK 33016 cells. The solid grey columns show the results with the human pol I promoter, the cross-hatched columns show the results with the FL canine pol I promoter, the dotted columns show the results with the MID canine pol I promoter and the vertically hatched columns show the results with the SHORT canine pol I promoter. "A" indicates LUC and viral polymerase, "B" indicates LUC and infection (MOI=0.05) and "C" indicates LUC. The y-axis indicates relative light units (RLU).

FIG. 4 shows that all tested fragments of the canine pol I promoter can drive expression of the luc transgene in MDCK cells. Furthermore, FIG. 5 demonstrates that the full-length human pol I promoter is able to drive expression of the transgene in MDCK cells and is even more efficient than the canine pol I promoter.

Figure 6:
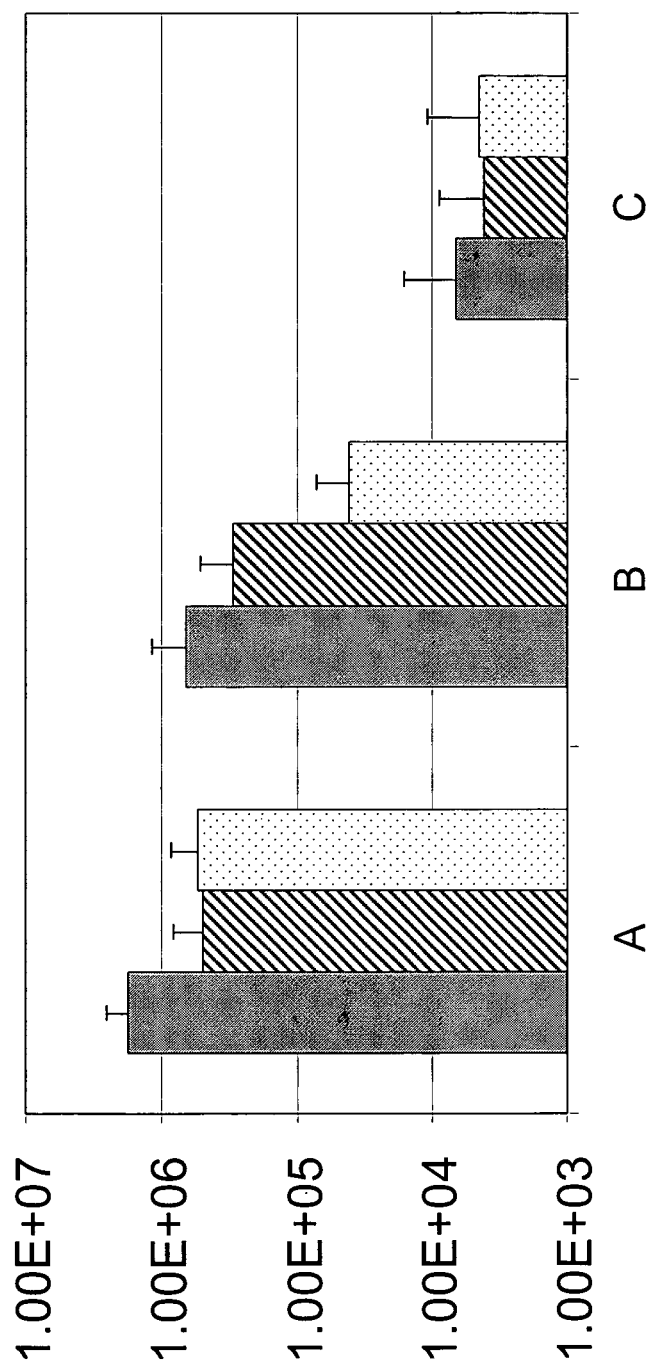
FIG. 6 shows a comparison of the activity of the FL and SHORT human pol I promoter and the full-length canine pol I promoter in MDCK cells 33016 cells. The solid grey columns show the results with the full-length human promoter, the hatched columns show the results with the full-length canine promoter and the dotted columns show the results with the short human pol I promoter. A indicates LUC+polymerasse, B indicates LUC+infection and C shows LUC only. The y-axis indicates relative light units (RLU).

In order to further define the region of the human pol I promoter which is necessary to drive expression of the transgene, the experiment was repeated with a fragment of the human pol I promoter as shown in FIG. 2 ("short" pol I). It was found that, while the full length pol I promoter is more active, the full-length as well as the short human pol I promoter are active in MDCK cells (FIG. 6).

The constructs containing the human and canine pol I promoter sequences were further transfected into MDCK from ATCC and MDCK 33016 cells [18] in Order to determine whether the activity of the human pol I promoter is restricted to a certain cell line. As shown in FIG. 7, the human pol I promoter was able to drive expression of the transgene in both cell types but the expression was more efficient in MDCK 33016 cells. Rescuing influenza virus from MDCK cells using human pol I promoter The efficiency of influenza virus rescue using the human pol I promoter was compared in MDCK and 293T cells. The influenza viral genome was cloned into pHW2000 expression vectors [69]. This vector contains a fragment of the human pol I promoter which was shown to be active in MDCK cells (see FIG. 5). In particular, the following vectors were used: pHW-WSN PA (0.534 µg/µl); pHW-WSN PB1 (0.432 µg/µl); pHW-WSN PB2 (0.357 µg/µl); pHW-WSN NP (0.284 µg/µl); pHW-WSN NS (0.217 µg/µl); pHW-WSN M (0.232 µg/µl); pHW-WSN HA (0.169 µg/µl); pHW-WSN NA (0.280 µg/µl) and pcDNA-TMPRSS (0.775 µg/µl; encoding serine protease). Protein-coding genes were controlled by a cytomegalovirus (CMV) promoter.

For the virus rescue, 293T cells were seeded at a density of $5 \times 10^6$ cells/well in 6-well dishes with 2 ml of Dulbecco's Modified Eagle Medium (DMEM) with 10% FCS. MDCK cells were plated at $0.3 \times 10^6$ cell/well in 6-well dished with 2 ml of medium. The cells were incubated overnight at 37° C. and were transfected when they had reached a confluency of 50-80%.

293T and MDCK cells were transfected using FuGENE 6 Transfection Reagent (Roche Cat.#11988387001) and Lipofectamine LTX Plus Reagent (Invitrogen Cat.#15338-100), respectively. The cells were transfected with 1 µg of each vector in accordance with the following protocols. For FuGENE 6, the reagent (3 µl of FuGENE/µg DNA) was diluted in 73 µl serum-free medium (without antibiotics), mixed gently and incubated at room temperature for 5 minutes. Afterwards the DNA was added to each to the diluted FuGENE, mixed gently and incubated at room temperature for at least 15 minutes. The DNA/FuGENE complex was added drop wise to the 293T cells without removing the growth medium and the cells were incubated at 37° C. for 24 hours.

For transfection with lipofectamine, the reagent (25 µl) was diluted in 500 µl serum-free medium and incubated at room temperature for 5 minutes. The DNA was added and the mixture was incubated at room temperature for 30 minutes. Following incubation, 500 µl of serum-free medium was added drop wise to the transfection reagent after the growth medium had been removed from the cells. The cells were subsequently incubated at 37° C. for 24 hours. 24 hours after transfection, the medium was changed.

Two days after infection, the supernatant from the cells was collected by centrifugation at 1000 rpm for 5 minutes. The virus collected in the supernatant was used for Focus-Forming Assays. Furthermore, the infected cells were lysed and used for Western Blot analysis.

Western Blot Analysis

The 293T and MDCK cells were lysed and subjected to Western Blot analysis in accordance with standard protocols. Antibodies against the M and NP protein were used to detect these proteins on the membrane. Antibodies against S6 were used as a loading control. The lanes labelled as 'WSN' were loaded with proteins from the rescued virus. The lanes labelled 'M' and 'NP' contain recombinant M and NP proteins as a control. As these recombinant proteins were expressed from a different gene they migrate slightly slower in the gel.

Figure 8:
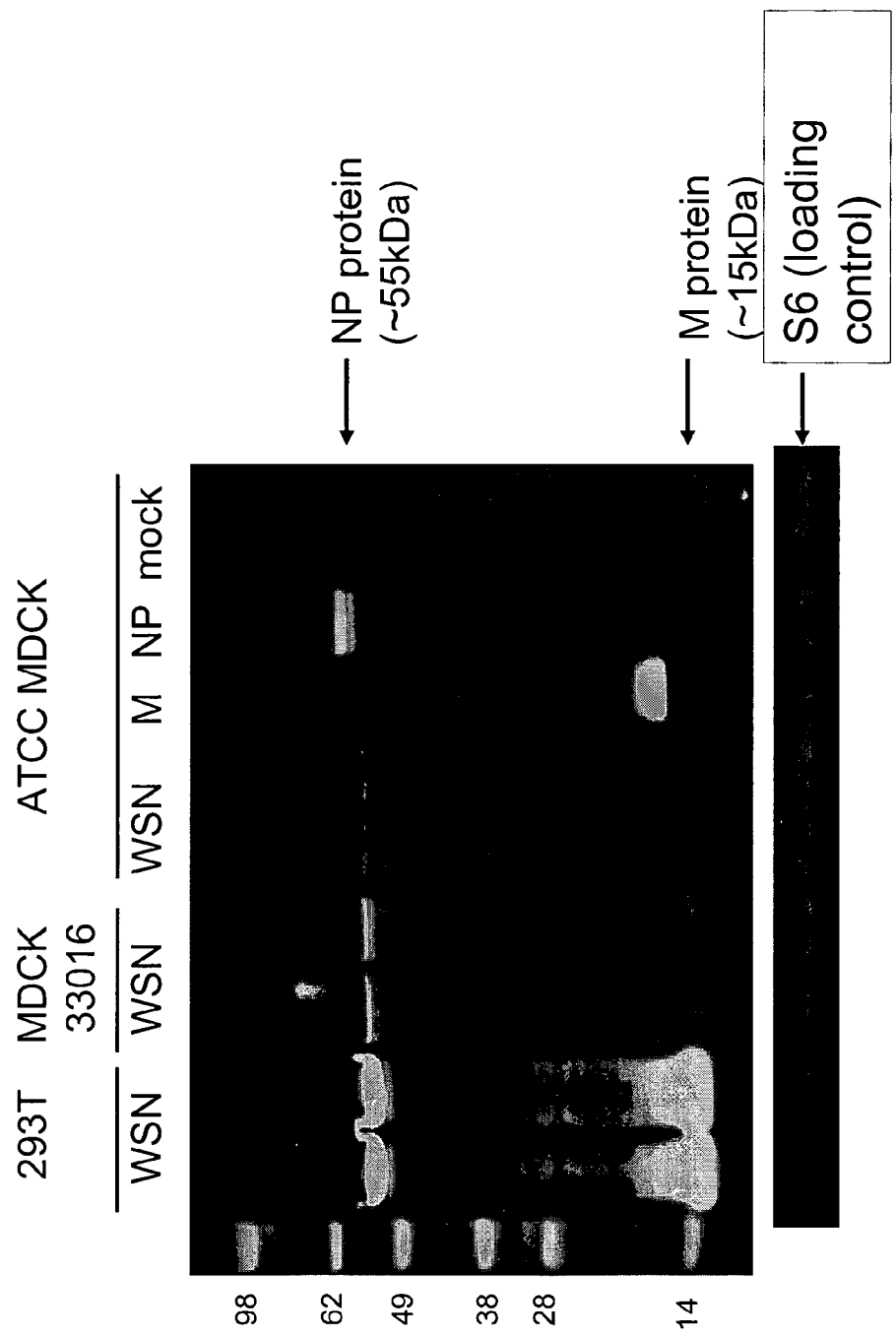
FIG. 8 shows a western blot analysis of M and NP proteins in cell lysates after virus rescue.

The results of the analysis are shown in FIG. 8 where it is evident that the expression construct under control of the human pol I promoter allows viral rescue in 293T as well as in MDCK cells.

Focus-Forming Assays

Uninfected MDCK cells were plated at a density of 6.25× $10^4$ cells/well in 48 well plates in 500 µl of DMEM with 10% FCS. The next day cells were infected with viruses in a volume of 100-150 µl for 2 hours at 37° C. The cells were thereby infected with various dilutions of the virus. Two hours post-infection, the medium was aspirated and 5000 of DMEM with 10% FCS was added to each well. The cells were incubated at 37° C. until the next day.

24 hours after infection, the medium was aspirated and the cells washed once with PBS. 500 µl of ice-cold 80% acetone in PBS was added to each well followed by incubation at 4° C. for 30 minutes. The acetone mix was aspirated and the cells washed once with PBST (PBS+0.1% Tween). 500 µl of 2% BSA in PBS was added to each well followed by incubation at room temperature (RT) for 30 minutes. 500 µl of a 1:6000 dilution of anti-NP was added in blocking buffer followed by incubation at RT for 2 hours. The antibody solution was aspirated and the cells washed twice with PBST. Secondary antibody (goat anti mouse) was added at a dilution 1:2000 in 500 µl blocking buffer and the plate was incubated at RT for 2 hours. The antibody solution was aspirated and the cells washed three times with PBST. 500 µl of KPL True Blue was added to each well and incubated for 10 minutes. The reaction was stopped by aspirating the True-Blue and washing once with $dH_2O$. The water was aspirated and the cells left to dry.

Figure 9:
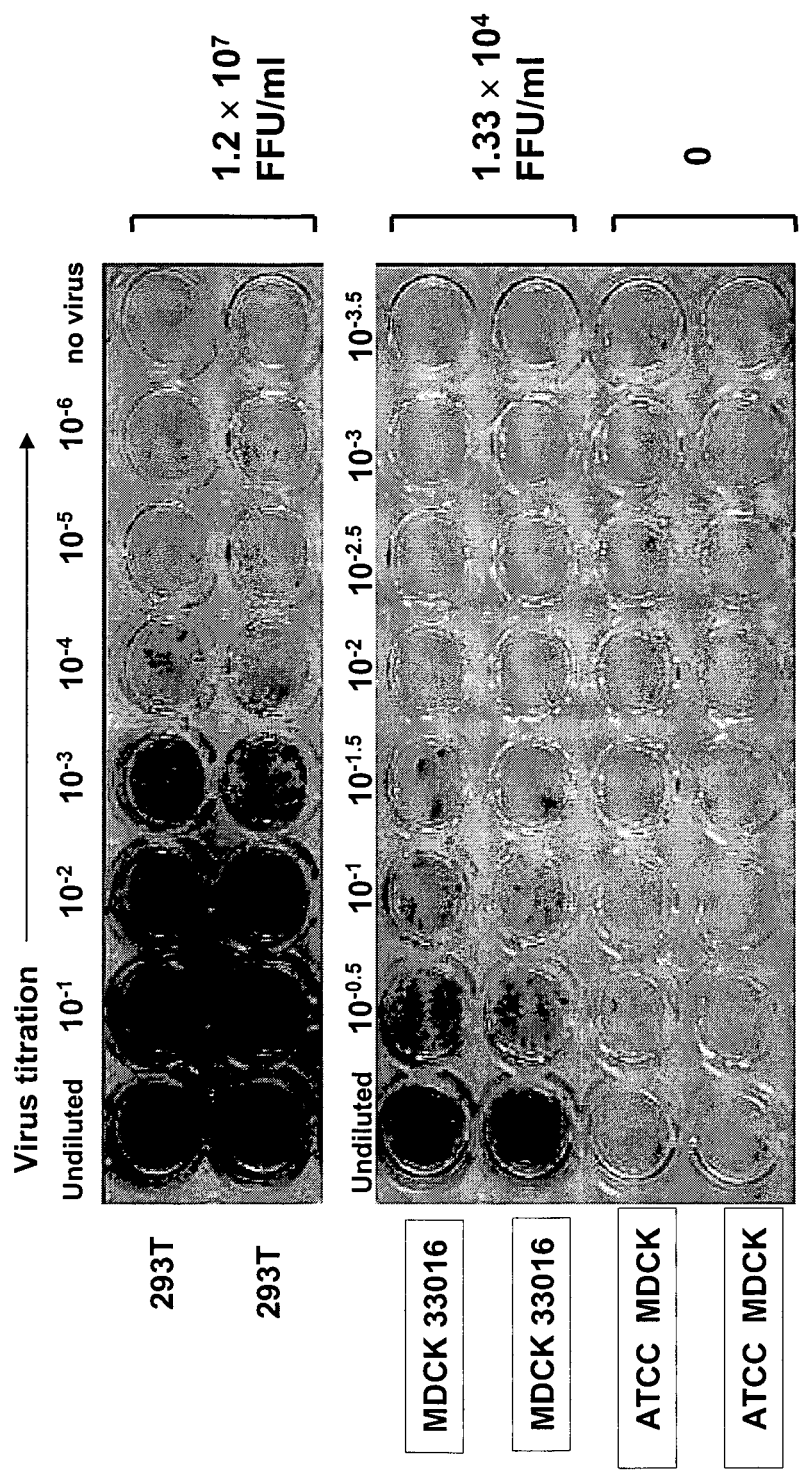
FIG. 9 shows results of a focus-forming assay using supernatant from cells infected with reverse genetics constructs.
Figure 10:
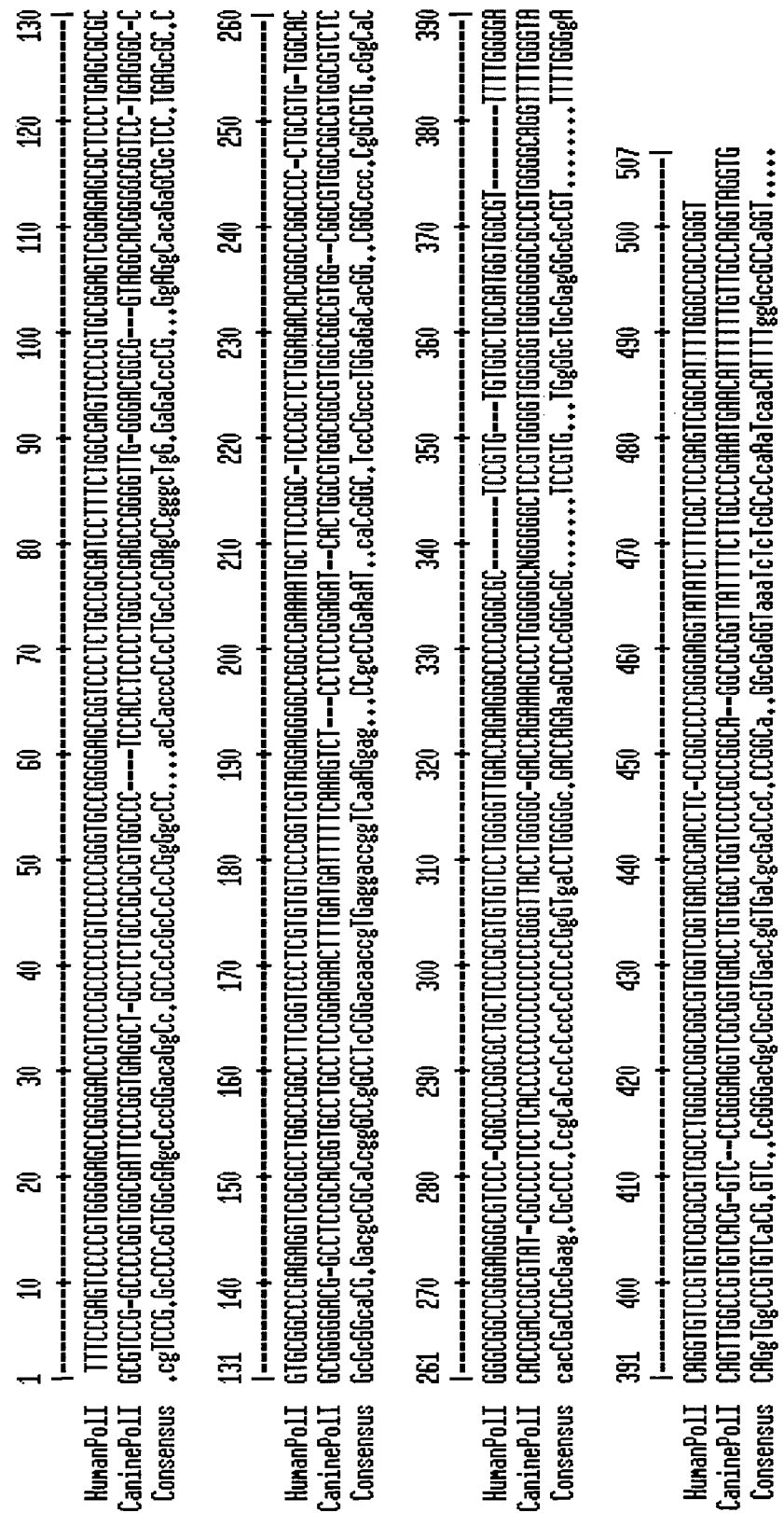
FIG. 10 shows an alignment of DNA sequences of human and canine pol I promoters (SEQ ID NOs 1 and 3, respectively).

The results of the assay are shown in FIG. 9 which demonstrates clearly that infectious virus was obtained from 293T as well as MDCK cells.

Virus rescue of the A/Puerto Rico/8/34 influenza strain using a human pol I reverse genetics system was also tested in MDCK ATCC, MDCK 33016-PF and 293T cells as described in reference 70. Experiments were performed in which the virus was rescued in the presence and absence of the helper plasmid TMPRSS2 which encodes a serine protease. Furthermore, the viral rescue was performed with and without the addition of feeder cells 24 hours after the viral rescue. The results are shown in FIG. 12 and demonstrate that efficient viral rescue could be achieved in MDCK cells under various conditions using the human pol I promoter.

Figure 13:
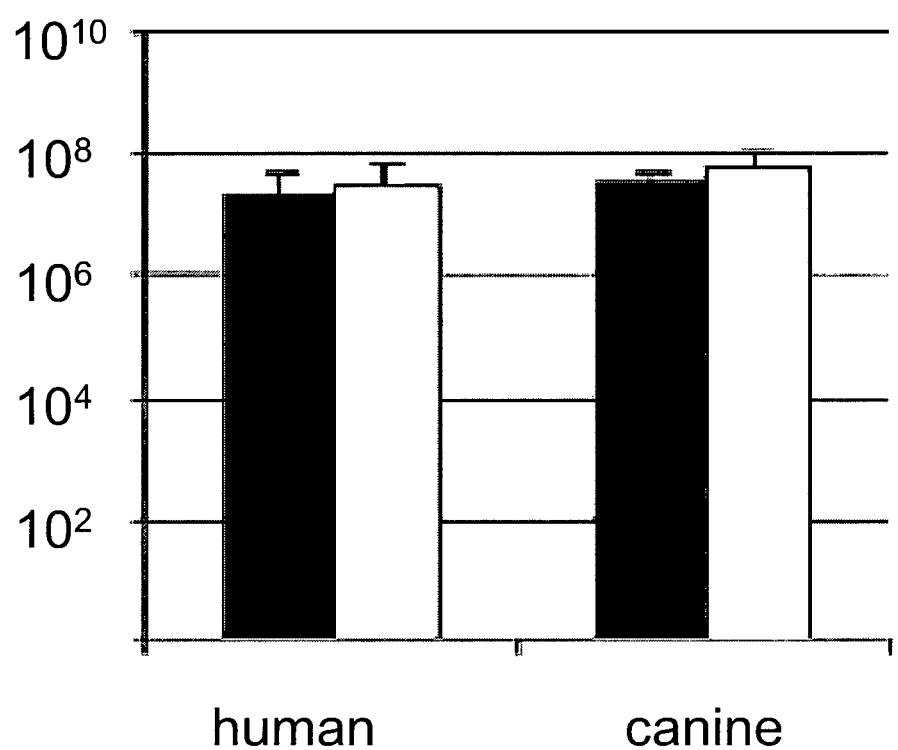
FIG. 13 compares the rescue of the A/Puerto Rico/8/34 influenza strain by human or canine pol I-driven reverse genetics in MDCK 33016-PF cells. The black columns show the results in the absence of the TMPRSS2 helper plasmid and the white bars show the result in the presence of the TMPRSS2 helper plasmid. The y-axis represents the virus titre (ffu/mL).

To compare whether the efficiency of viral rescue in MDCK 33016-PF using a human pol I promoter is comparable with the rescue using a canine pol I promoter, the cells were transfected with a human pol I RG system or a canine pol I RG system as described in reference 70. The experiments were performed in the presence and absence of the TMPRSS helper plasmid. The results (FIG. 13) demonstrate that the A/Puerto Rico/8/34 strain was rescued with comparable efficiency to the canine pol I system when the human pol I system was used.

It will be understood that the invention has been described by way of example only and modifications may be made whilst remaining within the scope and spirit of the invention.

DEPOSIT INFORMATION

A deposit of the microorganism MDCK 33016 (DSM ACC2219) was deposited on Jun. 7, 1995 according to the Budapest Treaty in the International Depository Authority DSM-Deutsche Sammlung Von Mikroorganismen and Zellkulturen GmbH, Mascheroder Weg 1b, D-38124 Braunschweig.

REFERENCES

[1] WO2007/002008
[2] WO2007/124327
[3] Koudstaal et al. (2009) Vaccine 272588-2593
[4] WO2009/000891
[5] Sambrook et al, Molecular Cloning: A Laboratory Manual, 2 ed., 1989, Cold Spring Harbor Press, Cold Spring Harbor, N.Y.
[6] Racaniello and Baltimore (1981) Science 214:916-919
[7] Kaplan et al. (1985) Proc Natl Acad Sci USA 82: 8424-8428
[8] Fodor et al. (1999) J. Virol 73(11):9679-9682
[9] Hoffmann et al. (2002) Proc Natl Acad Sci USA 99: 11411-11416
[10] Kobayashi et al. (2007) Cell Host Microbe 19; 1(2):147-57
[11] Stech et al. (2008) Nucleic Acids Res 36(21):e139
[12] Kistner et al. (1998) Vaccine 16:960-8
[13] Kistner et al. (1999) Dev Biol Stand 98:101-110
[14] Bruhl et al. (2000) Vaccine 19:1149-58
[15] Pau et al. (2001) Vaccine 19:2716-21
[16] http://www.atcc.org/
[17] http://locus.umdnj.edu/
[18] WO97/37000
[19] Brands et al. (1999) Dev Biol Stand 98:93-100
[20] Halperin et al. (2002) Vaccine 20:1240-7
[21] EP-A-1260581 (WO01/64846)

[22] WO2006/071563
[23] WO2005/113758
[24] WO97/37001
[25] Neumann et al. (2005) Proc Natl Acad Sci USA 102: 16825-9
[26] WO02/28422
[27] WO02/067983
[28] WO02/074336
[29] WO01/21151
[30] WO02/097072
[31] WO2005/113756
[32] Vaccines. (eds. Plotkins & Orenstein). 4th edition, 2004, ISBN: 0-7216-9688-0
[33] Huckriede et al. (2003) *hods Enzymol* 373:74-91
[34] Treanor et al. (1996) *J Infect Dis* 173:1467-70
[35] Keitel et al. (1996) *Clin Diagn Lab Immunol* 3:507-10
[36] Herlocher et al. (2004) *J Infect Dis* 190(9): 1627-30
[37] Le et al. (2005) *Nature* 437(7062):1108
[38] WO2008/068631
[39] Gennaro (2000) *Remington: The Science and Practice of Pharmacy.* 20th edition, ISBN: 0683306472
[40] Banzhoff (2000) *Immunology Letters* 71:91-96
[41] Nony et al. (2001) *Vaccine* 27:3645-51
[42] EP-B-0870508
[43] U.S. Pat. No. 5,948,410
[44] WO2007/052163
[45] WO2007/052061
[46] WO90/14837
[47] Podda & Del Giudice (2003) *Expert Rev Vaccines* 2:197-203
[48] Podda (2001) *Vaccine* 19: 2673-2680
[49] *Vaccine Design: The Subunit and Adjuvant Approach* (eds. Powell & Newman) Plenum Press 1995 (ISBN 0-306-44867-X)
[50] *Vaccine Adjuvants: Preparation Methods and Research Protocols* (Volume 42 of *Methods in Molecular Medicine* series). ISBN: 1-59259-083-7. Ed. O'Hagan
[51] WO2008/043774
[52] Allison & Byars (1992) *Res Immunol* 143:519-25
[53] Hariharan et al. (1995) *Cancer Res* 55:3486-9
[54] US-2007/014805
[55] US-2007/0191314
[56] Suli et al. (2004) *Vaccine* 22(25-26):3464-9
[57] WO95/11700
[58] U.S. Pat. No. 6,080,725
[59] WO2005/097181
[60] WO2006/113373
[61] Potter & Oxford (1979) *Br Med Bull* 35: 69-75
[62] Greenbaum et al. (2004) *Vaccine* 22:2566-77
[63] Zurbriggen et al. (2003) *Expert Rev Vaccines* 2:295-304
[64] Piascik (2003) *J Am Pharm Assoc* (Wash D.C.). 43:728-30
[65] Mann et al. (2004) *Vaccine* 22:2425-9
[66] Halperin et al. (1979) *Am J Public Health* 69:1247-50
[67] Herbert et al. (1979) *J Infect Dis* 140:234-8
[68] Chen et al. (2003) *Vaccine* 21:2830-6
[69] Hoffmann et al. (2000) *Proc Natl Acad Sci USA* 97:6108
[70] Suphaphiphat et al. (2010) J. Virol. 84(7) 3721-3725

The invention claimed is:

1. A method for producing a recombinant virus, comprising a step of growing a canine kidney host cell comprising at least one expression construct encoding a viral RNA molecule, wherein expression of the viral RNA molecule from the construct is controlled by a human pol I promoter under conditions where the viral RNA molecule is expressed in order to produce virus.

2. A method of preparing a virus, comprising steps of: (i) producing a recombinant virus by the method of claim 1; (ii) infecting a culture host with the virus obtained in step (i); (iii) culturing the host from step (ii) to produce further virus; and (iv) purifying virus obtained in step (iii).

3. A method for preparing a vaccine, comprising steps of (a) preparing virus by the method of claim 2 and (b) preparing vaccine from the virus.

4. The method of claim 3, wherein step (b) comprises formulating the vaccine with an adjuvant.

5. The method of claim 4, wherein the adjuvant comprises a terpenoid.

6. The method of claim 5, wherein the terpenoid is squalene or saponin.

7. The method of claim 4, wherein the adjuvant comprises an oil-in-water emulsion.

8. The method of claim 7, wherein the oil-in-water emulsion adjuvant comprises squalene, polysorbate 80, and sorbitan trioleate.

9. The method of claim 8, wherein the squalene, polysorbate 80, and sorbitan trioleate are in a relative weight ratio to each other of about 4.3:0.5:0.48.

10. The method of claim 1 wherein the canine kidney cell is an MDCK cell.

11. The method of claim 10 wherein the MDCK cell is cell line MDCK 33016 (DSM ACC2219).

12. The method of claim 1, wherein the canine kidney cell includes at least one bi-directional expression construct.

13. The method of claim 1, wherein the expression construct is an expression vector or a linear expression construct.

14. The method of claim 1, wherein the human pol I promoter comprises the sequence of SEQ ID NO: 1 or SEQ ID NO: 2.

15. The method of claim 1, wherein the virus is a segmented virus.

16. The method of claim 1, wherein the virus is a non-segmented virus.

17. The method of claim 1, wherein the virus is a negative-strand RNA virus.

18. The method of claim 17, wherein the virus is influenza virus.

19. A canine kidney host cell for producing a virus comprising at least one expression construct encoding a viral RNA molecule, wherein expression of the viral RNA molecule from the construct is controlled by a human pol I promoter.

20. A canine kidney cell for producing a virus having at least one endogenous pol I promoter which control(s) expression of endogenous rRNA and at least one non-endogenous human pol I promoter which control(s) expression of a viral RNA or the complement thereof.

\* \* \* \* \*

SEQUENCE LISTING

```
<160> NUMBER OF SEQ ID NOS: 9

<210> SEQ ID NO 1
<211> LENGTH: 499
<212> TYPE: DNA
<213> ORGANISM: Homo sapiens

<400> SEQUENCE: 1
tttccgagtc cccgtgggga gccggggacc gtcccgcccc cgtcccccgg gtgccgggga      60
gcggtccccg ggccgggccg cggtccctct gccgcgatcc tttctggcga gtccccgtgc     120
ggagtcggag agcgctccct gagcgcgcgt gcggcccgag aggtcgcgcc tggccggcct     180
tcggtccctc gtgtgtcccg gtcgtaggag gggccggccg aaaatgcttc cggctcccgc     240
tctggagaca cgggccggcc cctgcgtgt ggcacgggcg gccgggaggg cgtccccggc      300
ccggcgctgc tcccgcgtgt gtcctggggt tgaccagagg gccccgggcg ctccgtgtgt     360
ggctgcgatg gtggcgtttt tggggacagg tgtccgtgtc gcgcgtcgcc tgggccggcg     420
gcgtggtcgg tgacgcgacc tcccggcccc gggggaggta tatctttcgc tccgagtcgg     480
cattttgggc cgcccgggt                                                  499

<210> SEQ ID NO 2
<211> LENGTH: 219
<212> TYPE: DNA
<213> ORGANISM: Homo sapiens

<400> SEQUENCE: 2
gccgggaggg cgtccccggc ccggcgctgc tcccgcgtgt gtcctggggt tgaccagagg      60
gccccgggcg ctccgtgtgt ggctgcgatg gtggcgtttt tggggacagg tgtccgtgtc     120
gcgcgtcgcc tgggccggcg gcgtggtcgg tgacgcgacc tcccggcccc gggggaggta    180
```

```
tatctttcgc tccgagtcgg cattttgggc cgcccgggt                            219
```

```
<210> SEQ ID NO 3
<211> LENGTH: 1814
<212> TYPE: DNA
<213> ORGANISM: Canis spec.
<220> FEATURE:
<221> NAME/KEY: misc_feature
<222> LOCATION: 1647
<223> OTHER INFORMATION: n = A,T,C or G

<400> SEQUENCE: 3
agcgtgagca ggagaattct ggagaaacag attgtgttat aagaaagaaa gaaagaaaga     60
aagaaagaaa gaaagagaaa atccttatgt tctttgagcc tcccctcccc cccagaattg    120
agttcctctt ccacgacctc ttctcattca acccaataga caagtatttg gggggggggg    180
gtcaggtccc agacgcttaa agggtggaag tgaaagtggt gcggggaag ggggggggca     240 caccgtcctc tccagcgcct ttggttcaaa cctccttcgt gacctccctc cctccctccc    300
tccttcgtct tataaatata taaataaaat cctaaagaaa aagaaaaaaa aaaaaaaaaa    360
aaaggaagga cacgagaaaa aacggtgcat ccgttgccgt cctaagagtc ctcgcctggt    420
ttcggctcta cgttccctcc ctgacctcgg aaacgtgcct gagtcgtccc gggagccccg    480
cgcggcgagc gcgaccccct ttccgggcgg cagcgggccc ggacggacgg acggacggac    540
ggacgggttt tccaaggctc ccccgccccg ggaggacggg ggttcgcgcg gtgcgcggcc    600
gtgtgctccc ggggccctcc gccgtccccg ggccgagagg cgagatccga ggcgccctga    660
cggcctcgcc gccggatct gtcccgctgt cgttcgcgcc ggttgtcggg tgccacctgg    720
cggccgcttt tatagagcgt gtcccctccg gaggctcggc ggcgacaggc aaggaacagc    780
tttggtgtcg gtttcccggg gccgagttcc aggaggaggg cggctccggc gcgagcgtcc    840
ggctgtcgcc ggggcctcgg cgcgcgatgc gctcgccgga gattggacct ccggagctgc    900
gagggagtgt cgccgtcgcc gctgtcgccg ctgtcgcctc cgcctcgctc ccggaggagg    960
ccgtgcgggc cgcctgggtg ggtcgaccag cacccgccgg tggctcctcc tccgcccgcg   1020
cggaccgacc tgggccgcct cggggcgggg ggacaggggtg tgtcccgccg tccgtcctgt   1080
ggctccgggc gatcttcggg ccttccttcc gtgtcactcg gttgtctccc gtggtcacgc   1140
cctggcgacg ggaccggtc tgagcctgga ggggaagccc gtgggtggcg cgacagaccc    1200
ggctgcgggc acgtgtgggg gtcccgggcg tcggacgcga ttttctcccc ttgttccgag   1260
gcccgctgcg gaggtgggtc ccgggcggtc ggaccgggtg ccacgcgggg gtgggcgggc   1320
cgtccgttcg ggcgtccggc cccggtggcg attcccggtg aggctgcctc tgccgcgcgt   1380
ggccctccac ctcccctggc ccgagccggg gttggggacg gcggtaggca cggggcggtc   1440
ctgagggccg cggggacgg cctccgcacg gtgcctgcct ccggagaact ttgatgattt     1500
ttcaaagtct cctcccggag atcactggcg tggcggcgtg gcggcgtggc ggcgtggcgg   1560
cgtggcgtct ccaccgaccg cgtatcgccc ctcctcaccc ccccccccc ccgggttacc    1620 tggggcgacc agaaagccct gggggcnggg ggctccgtgg ggtgggggtg gggggcgcc    1680 gtggggcagg ttttgggtac agttggccgt gtcacggtcc cggaggtcg cggtgacctg    1740 tggctggtcc ccgccggcag gcgcggttat tttcttgccc gaaatgaaca ttttttgttg   1800
ccaggtaggt gctg                                                     1814
```

```
<210> SEQ ID NO 4
<211> LENGTH: 474
```

```
<212> TYPE: DNA
<213> ORGANISM: Canis spec.
<220> FEATURE:
<221> NAME/KEY: misc_feature
<222> LOCATION: 307
<223> OTHER INFORMATION: n = A,T,C or G

<400> SEQUENCE: 4
cccggtggcg attcccggtg aggctgcctc tgccgcgcgt ggccctccac ctcccctggc     60
ccgagccggg gttggggacg gcggtaggca cggggcggtc ctgagggccg cggggggacgg   120 cctccgcacg gtgcctgcct ccggagaact ttgatgattt ttcaaagtct cctcccggag   180
atcactggcg tggcggcgtg gcggcgtggc ggcgtggcgg cgtggcgtct ccaccgaccg   240
cgtatcgccc ctcctcaccc cccccccccc ccggggttacc tggggcgacc agaaagccct  300
gggggcnggg ggctccgtgg ggtggggggtg ggggggcgcc gtgggcaggc ttttgggtac  360
agttggccgt gtcacggtcc cgggaggtcg cggtgacctg tggctggtcc ccgccggcag  420
gcgcggttat ttcttgccc gaaatgaaca ttttttgttg ccaggtaggt gctg           474

<210> SEQ ID NO 5
<211> LENGTH: 288
<212> TYPE: DNA
<213> ORGANISM: Canis spec.
<220> FEATURE:
<221> NAME/KEY: misc_feature
<222> LOCATION: 121
<223> OTHER INFORMATION: n = A,T,C or G

<400> SEQUENCE: 5
ggcgtggcgg cgtggcggcg tggcggcgtg gcggcgtggc gtctccaccg accgcgtatc    60
gcccctcctc accccccccc cccccgggt tacctggggc gaccagaaag ccctgggggc   120 nggggggctcc gtggggtggg ggtgggggggg cgccgtgggc aggttttggg gtacagttgg  180
ccgtgtcacg gtcccgggag gtcgcggtga cctgtggctg gtccccgccg gcaggcgcgg  240 ttatttttctt gcccgaaatg aacattttttt gttgccaggt aggtgctg               288

<210> SEQ ID NO 6
<211> LENGTH: 566
<212> TYPE: PRT
<213> ORGANISM: Influenza A virus

<400> SEQUENCE: 6

Met Lys Ala Ile Leu Val Val Leu Leu Tyr Thr Phe Ala Thr Ala Asn
 1               5                   10                  15

Ala Asp Thr Leu Cys Ile Gly Tyr His Ala Asn Asn Ser Thr Asp Thr
                20                  25                  30

Val

```
Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
                195                 200                 205

Tyr Gln Asn Ala Asp Thr Tyr Val Phe Val Gly Ser Ser Arg Tyr Ser
            210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
```

```
                       545                 550                 555                 560

Gln Cys Arg Ile Cys Ile
                565

<210> SEQ ID NO 7
<211> LENGTH: 566
<212> TYPE: PRT
<213> ORGANISM: Influenza A virus

<400> SEQUENCE: 7

Met Lys Ala Lys Leu Leu Val Leu Leu Cys Ala Leu Ser Ala Thr Asp
  1               5                  10                  15

Ala Asp Thr Ile Cys Ile Gly Tyr His Ala Asn Asn Ser Thr Asp Thr
                 20                  25                  30

Val Asp Thr Val Leu Glu Lys Asn Val Thr Val Thr His Ser Val Asn
             35                  40                  45

Leu Leu Glu Asp Asn His Asn Gly Lys Leu Cys Lys Leu Lys Gly Ile
         50                  55                  60

Ala Pro Leu Gln Leu Gly Lys Cys Ser Ile Ala Gly Trp Ile Leu Gly
 65                  70                  75                  80

Asn Pro Glu Cys Glu Ser Leu Phe Ser Lys Lys Ser Trp Ser Tyr Ile
                 85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350
```

Phe Ile Glu Gly Gly Trp Thr Gly Met Ile Asp Gly Trp Tyr Gly Tyr
            355                 360                 365

His His

```
Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 9
<211> LENGTH: 470
<212> TYPE: PRT
<213> ORGANISM: Influenza A virus
<400> SEQUENCE: 9

Met Asn Pro Asn Gln Lys Ile Ile Thr Ile Gly Ser Ile Cys Met Thr
 1               5                  10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
```

```
                50                  55                  60
Thr Tyr Val Asn Ile Asn Asn Thr Asn Val Val Ala Gly Lys Asp Thr
 65                  70                  75                  80

Thr Ser Val Thr Leu Ala Gly Asn Ser Ser Leu Cys Pro Ile Arg Gly
                 85                  90                  95

Trp Ala Ile Tyr Ser Lys Asp Asn Ser Ile Arg Ile Gly Ser Lys Gly
                100                 105                 110

Asp Val Phe Val Ile Arg Glu Pro Phe Ile Ser Cys Ser His Leu Glu
                115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
                180                 185                 190

Ile Gly Ile Ser Gly Pro Asp Asp Gly Ala Val Ala Val Leu Lys Tyr
                195                 200                 205

Asn Gly Ile Ile Thr Glu Thr Ile Lys Ser Trp Arg Lys Arg Ile Leu
210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
                245                 250                 255

Lys Ile Glu Lys Gly Lys Ile Thr Lys Ser Ile Glu Leu Asp Ala Pro
                260                 265                 270

Asn Ser His Tyr Glu Glu Cys Ser Cys Tyr Pro Asp Thr Gly Thr Val
                275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
                325                 330                 335

Pro Val Thr Val Asp Gly Ala Asp Gly Val Lys Gly Phe Ser Tyr Arg
                340                 345                 350

Tyr Gly Asn Gly Val Trp Ile Gly Arg Thr Lys Ser Asn Ser Ser Arg
                355                 360                 365

Lys Gly Phe Glu Met Ile Trp Asp Pro Asn Gly Trp Thr Asp Thr Asp
                370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Arg Pro Arg
                420                 425                 430

Glu Gly Thr Thr Val Trp Thr Ser Gly Ser Ser Ile Ser Phe Cys Gly
                435                 440                 445

Val Asn Ser Asp Thr Ala Asn Trp Ser Trp Pro Asp Gly Ala Glu Leu
450                 455                 460
```

```
Pro Phe Thr Ile Asp Lys
465                 470
```